US008435571B2

(12) United States Patent
Pretorius

(10) Patent No.: US 8,435,571 B2
(45) Date of Patent: May 7, 2013

(54) EXTRACTS AND COMPOUNDS FROM "AGAPANTHUS AFRICANUS" AND THEIR USE AS BIOLOGICAL PLANT PROTECTING AGENTS

(75) Inventor: Johannes Christiaan Pretorius, Bloemfontein (ZA)

(73) Assignees: Afrarforum AG, Bomlitz (DE); Agrarforum SA (Pty.) Ltd., Universitas (ZA)

( * ) Notice: Subject to any disclaimer, the term of this patent is extended or adjusted under 35 U.S.C. 154(b) by 0 days.

(21) Appl. No.: 12/985,691

(22) Filed: Jan. 6, 2011

(65) Prior Publication Data

US 2012/0015062 A1    Jan. 19, 2012

Related U.S. Application Data

(62) Division of application No. 11/993,142, filed as application No. PCT/EP2006/006104 on Jun. 24, 2006, now abandoned.

(30) Foreign Application Priority Data

Jun. 30, 2005 (EP) .................................... 05014247
Jun. 30, 2005 (EP) .................................... 05014265

(51) Int. Cl.
*A61K 36/00* (2006.01)
(52) U.S. Cl.
USPC ......................................... 424/725; 424/778
(58) Field of Classification Search .................. 424/725, 424/778
See application file for complete search history.

(56) References Cited

U.S. PATENT DOCUMENTS 5,212,165 A     5/1993  Aberg et al.
2009/0258097 A1  10/2009  Pretorius

FOREIGN PATENT DOCUMENTS

AU        2004201516 A1 *  5/2004

OTHER PUBLICATIONS

Arbel et al. An Antifungal Substance Isolated From a Local Plant; Bull. Res. Counc. of Israel, vol. 9E, 1961, pp. 152-154 in view of AUSU.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Duncan of al., Journal of Ethnopharmacology 68: 63-70 (1999).
Wikipedia: Caryophyllaceae: online, URL<http://en.wikipedia.or/wiki/Caryophyllaceae> pp. 1-4 accessed Feb. 4, 2010.
Wikipedia: Dianthus: online, URL<http://en.wikipedia.or/wiki/Dianthus> pp. 1-2 accessed Feb. 4, 2010.

* cited by examiner

*Primary Examiner* — Patricia Leith
(74) *Attorney, Agent, or Firm* — Perkins Coie LLP

(57) ABSTRACT

The invention relates to plant extracts, especially based on species of the genus *Agapanthus* and combinations thereof with other extracts deriving from other plants. The invention further relates to the isolation, purification and identification of compounds in these extracts. The plant extracts and the isolated substances show significant antimicrobial activity, especially antifungal activity, and bio-stimulatory efficacy, when applied to other plants in vitro and in vivo, including under field conditions. The products according to this invention are suitable to be used as plant protecting agents for many crops and economic plants as an alternative for chemical pesticides.

10 Claims, 4 Drawing Sheets

(A)

(B)

Figure 1:
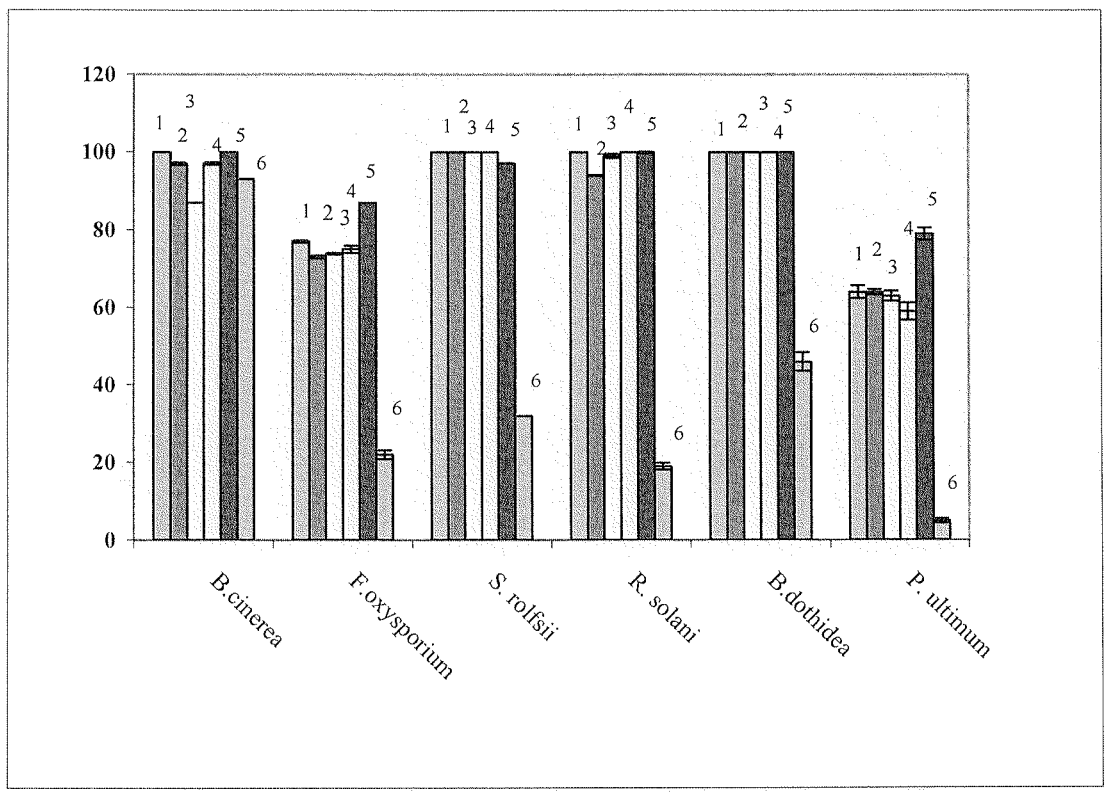

EXTRACTS AND COMPOUNDS FROM "AGAPANTHUS AFRICANUS" AND THEIR USE AS BIOLOGICAL PLANT PROTECTING AGENTS

This application is a divisional of U.S. application Ser. No. 11/993,142 filed Dec. 19, 2007, now abandoned which is a 371 of PCT/EP2006/006104 filed Jun. 24, 2006. The entire contents of the above-identified applications are hereby incorporated by reference.

This application claims priority to EP 05014247.0 filed Jun. 30, 2005 and EP 05014265.2 filed Jun. 30, 2005. The entire contents of the above-identified applications are hereby incorporated by reference.

TECHNICAL FIELD OF THE INVENTION

The invention relates to plant extracts, especially based on species of the genus *Agapanthus* and combinations thereof with other extracts deriving from other plants. The invention further relates to the isolation, purification and identification of compounds in these extracts. The plant extracts and the isolated substances show significant antimicrobial activity, especially antifungal activity, and bio-stimulatory efficacy, when applied to other plants in vitro and in vivo, including under field conditions. The products according to this invention are suitable to be used as plant protecting agents for many crops and economic plants as an alternative for chemical pesticides.

BACKGROUND OF THE INVENTION

Worldwide agriculture suffers, especially in developing countries such as in Africa, from annual huge losses of crop and other economic plants due to plant diseases. More than 30% of the food, fiber, feed and energy produced in crop production systems are destroyed by insects and diseases annually on a global scale. These yield losses are high as a result of low-input production systems due to the non-affordability of synthetic fungicides to farmers in developing countries that depend on non-conventional disease management practices often providing doubtful results.

In contrast, crop and plant producers in developed countries rely largely on synthetic pesticides to control plant diseases. It is an established fact that the use of synthetic chemical pesticides provides many benefits to crop producers. These benefits include higher crop yields, improved crop quality and increased food production for an ever increasing world population. The development of a wide range of chemicals with different formulations has enabled man to control a wide range of plant pathogens and substantially increased crop yields. More than a decade ago crop producers spent nearly $20 billion on pesticides and $150 million on other plant protection techniques, worldwide, to control pests in general. The world market share of fungicides alone was 20% in recent years whilst Europe accounted for 30% of the market. However, the same level of pathogen control has not been realized in developing countries, partly as a result of pesticide technology not being accessible to most resource poor farmers. Failure of modern approaches, technology and chemicals to reach farmers in developing countries is solely the result of high costs in relation to the value of the crops cultivated by these farmers. Consequently, crops are routinely subjected to attack from a wide spectrum of a diversity of pathogens and these farmers constantly experience serious crop damage. Moreover, yield losses are on the increase despite high pesticide usage, even in developed countries. Furthermore, control of plant diseases is not easily achieved with a single application of fungicide but requires frequent applications during the crop-growing period. However, synthetic pesticides may pose a couple of threats and hazards to the environment, especially when improperly used by farmers in developing countries who lack the technical skill of handling them, and who fail to adopt to this technology easily. This may result in undesirable residues left in food, water and the environment, and may cause toxicity to humans and animals, contamination of soils and groundwater and may lead to the development of crop pest populations that are resistant to treatment with agrochemicals. Especially sulfur and copper containing synthetic fungicides are toxic to mammals, wildlife and many beneficial insects.

Furthermore, in Africa and the Near East, obsolete pesticides have become a source of an additional great environmental concern. Some stocks are over 30 years old and are kept in poor conditions because of inadequate storage facilities and lack of staff trained in storage management. Obsolete pesticide stocks are potential time bombs. Leakage, seepage and various accidents related to pesticides are quite common and widespread.

Additionally, that frequent application of fungicides has resulted in fungal mutation and, subsequently new resistant strains (Khun, 1989, *Pesticide Science* 14:272-293), the combat of which usually requires stronger pesticides with again stronger impacts on the environment.

For all these reasons there is a considerable and increasing consumer resistance especially in the developed countries, initiated politically by the green parties, towards the use of synthetic chemicals/pesticides especially, supplying a rationale for a shift from chemical pesticides applications to the use of naturally derived plant protecting agents in order to reduce the pollution and health risk caused by pesticides.

As a result, research on the possible utilization of biological resources and its application potential in agriculture has become very relevant. A promising approach in this regard is the use of natural plant products as an interesting alternative to synthetic chemicals due to the apparent less negative impact on the environment.

This especially applies to the search for environmentally friendly bioactive naturally derived components and agents with, for example, broad-spectrum antimicrobial activity.

Natural products from plants are expected to have a narrow target range and highly-specific mode of action, to show limited field persistence, to have a shorter shelf life and present no residual threats. They are generally safer to humans and the environment than conventional synthetic chemical pesticides and can easily be adopted by farmers in developing countries who traditionally use plant extracts for the treatment of human diseases.

A further rationale for exploring the use of plant extracts or natural products as biological pesticides more extensively can be found in the plant itself. Plants have evolved highly specific chemical compounds that provide defense mechanisms against attack by disease causing organisms, including fungal attack, microbial invasion and viral infection (Cowan, 1999, *Clinical Microbiology Reviews* 12:564-582). These bioactive substances occur in plants as secondary metabolites, and have provided a rich source of biologically active compounds that may be used as novel crop-protecting agents. In nature some plants have the potential to survive very harsh environmental conditions. This has initiated the postulate that such plants might be utilized as sources for the development of natural products to be applied in agriculture by man as natural herbicides, bactericides, fungicides or products in crude or semipurified form. Secondary plant metabolites are distinct from primary metabolites in that they are generally non-essential for the basic metabolic processes such as respiration and photosynthesis. They are numerous and widespread, especially in higher plants and often present in small quantities (1-5%) as compared to primary metabolites (carbohydrates, proteins, lipids). Secondary metabolites are probably produced when required in the plant system and are synthesized in specialized cell types. Ecologically, secondary metabolites play essential roles in attracting pollinators, as adaptations to environmental stresses and serve as chemical defenses against insects and higher predators, micro-organisms and even other plants (allelochemicals).

Abiotic stress such as nutrient limitation, light intensity, water stress and others has been considered to trigger the formation of secondary metabolites. A biotic stress related type of plant-pathogen interaction involves the production of metabolites as part of a plant defense arsenal against microbial invasion and is considered disease determinants. Secondary metabolites with anti-microbial properties include terpenoids (e.g. iridoids, sesquiterpenoids, saponins), nitrogen- and/or sulphur containing (e.g. alkaloids, amines, amides), aliphatics (especially long-chain alkanes and fatty acids) and aromatics (e.g. phenolics, flavonoids, bi-benzyls, xanthones and benzoquinones).

Another related area of organic fanning systems is the potential to apply natural plant extracts as either plant growth regulators or bio-stimulants. Many natural plant compounds have been identified that affect the growth and development of plants. Secondary metabolites from plants may show also bio-stimulatory activities in plants, other plants included. Probably the most effective compound to enhance crop yield, crop efficiency and seed vigour has been identified as a brassinosteroid (Mandava, 1988, *Plant Physiology Plant Molecular Biology* 39:23-52). Brassionosteroids have also been identified as bio-stimulatory substances from a plant extract mixture deriving from a specific Pink species and a specific *Alfalfa* species (EP 1 051 075 B1). An elevated interest therefore exists to identify natural plant compounds with the ability to manipulate plant growth and development over a short period, e.g. a growing season.

An additional consideration is that plants whose extracts, for example show antimicrobial and/or bio-stimulatory properties, could be cultivated as alternative agricultural crops for serving as sources of active compounds in the production of natural pesticides or plant growth regulators.

Although plants are a valuable source for the development of new natural products with the potential to be used for disease management in organic crop production systems only a small number of plants has been investigated for possible use in plant disease control in agriculture. However, related to this relatively small number of investigated plants a relatively large number of scientific research activities has been done during the last couple of years. Some of them are listed as follows:

It was shown (Pretorius et al., 2002, *Annals of Applied Biology* 141:117-124) that mycelial growth inhibition was obtained with extracts from two species of the subclass Liliidae, namely *Aristea ecklonii* and *Agapanthus inapertus*. The crude extract of *A. ecklonii* performed best of all extracts as it totally inhibited the mycelial growth of all seven of the plant pathogenic test organisms and outperformed the inhibition by a broad spectrum synthetic fungicide (carbendazim/difenoconazole). Crude extracts of *A. inapertus* showed complete inhibition of four and strong inhibition of the remaining three plant pathogenic fungi.

Plant seeds also contain compounds with antimicrobial properties. Seed extracts of 50 plant species, belonging to different families, were evaluated for their ability to inhibit the growth of *Trichoderma viride* in vitro (Bharathimatha et al., 2002, *Acta Phytopathologica et Entomologica Hungarica* 37:75-82). Of the various seed extracts, that of *Harpullia cupanioides* (Roxb.), belonging to the family Sapindaceae, displayed very high antifungal activity.

The natural plant product Milsana®, extracted from the giant knotweed (*Reynoutria sacchalinensis*), is probably best known (Daayf, 1995, *Plant Disease* 79:577-580). The product has been reported to control powdery mildew, caused by *Sphaerotheca fuliginea*, in long English cucumber under greenhouse conditions and also showed broad spectrum activity against powdery mildew of tomato, apple and begonia as well as downy mildew of grapevine and rust of bean.

Extracts from the leaves and seed kernels of the neem tree (Ume et al., 2001, *The science and application of neem, meeting proceedings*, Glasgow, U.K. April-2001. Pp. 33-37) were tested for antifungal activity against the plant pathogenic fungus *Sclerotium rolfsii* [*Corticium rolfsii*]. All the extracts showed some effect against different growth stages of the fungus, but the effects were fungistatic rather than fungitoxic.

Amadioha (2002, *Archives of Phytopathology and Plant Protection* 35:37-42) evaluated the antifungal activities of the different extracts of *A. indica*. The oil extract from seeds as well as water and ethanol leaf extracts of the plant were effective in reducing the radial growth of *Cochliobolus miyabeanus* in culture and in controlling the spread of brown spot disease in rice.

A study directed towards identifying bio-stimulatory properties in plant extracts was performed by Cruz et al. (2002, *Acta Horticulturae* 569:235-238) by treating the roots of bean, maize and tomato with an aqueous leachate of *Callicarpa acuminate*. The aqueous extract of *C. acuminata* inhibited the radicle growth of tomato but had no effect on root growth of maize or beans.

According to Singh et al. (2001, *Journal of Crop Production* 4:121), allelochemicals isolated from some plants show strong bio-herbicidal activity at high concentrations, but at low concentrations these extracts can promote crop seed germination and seedling growth, hence showing a potential to be applied as bio-stimulatory agents or growth promoting substances in agriculture.

Extracts from some lucerne cultivars had a stimulatory effect in terms of seed germination as well as root and hypocotyl growth, whereas others showed the direct opposite effect, confirming that crop plants can also be affected by plant extracts aimed at controlling weed growth (Tran and Tsuzuki, 2002 *Journal of Agronomy and Crop Science* 188:2-7).

Leksomboon et al. (2001, *Kasetsart Journal, Natural Sciences* 35:392-396) demonstrated the antibacterial effect of leaf and other aqueous extracts of *Hibiscus sabdariffa, Psidium guajava, Punica granatum, Spondias pinnata* and *Tamarindus indica* against *Xanthomonas axonopodis*, the casual agent of citrus canker under both laboratory and field conditions.

Another natural product, carvone, derived from dill and caraway seed, has been developed to inhibit the growth of storage pathogens and to suppress sprouting of potatoes in the warehouse (Moezelaar et al., 1999, *In: Modern fungicides and antifungal compounds II; Intercept*

Limited, p. 453-467). Carvone is currently marketed as Talent® in the Netherlands.

In European patent EP 1 051 075 a preparation of a combination of species of the Pink family and species of *Alfalfa* is described (ComCat®) which reveals within a specific ratio a synergistic bio-stimulatory effect. ComCat® has demonstrated consistent plant growth enhancement and physiological efficiency in the treated plant's utilization of available nutrients. ComCat®, which enhances the health of vegetables, flowers and agricultural crops, is not a fertilizer substitute but, instead, it is a biological enhancer which stimulates the plant to more properly utilize available nutrients. Moreover, it activates and induces allelopathy and disease resistance in the treated plant and stimulates greater production of sugars, which are the building blocks for cellulose and fruiting bodies. The result is a more productive, healthier plant with stronger plant stalks, better flowering and greater fruit biomass (*Agraforum* Germany, 2002, Technical data sheet).

SUMMARY OF THE INVENTION

The invention provides extracts and preparations based on species of the genus *Agapanthus*, preferably *Agapanthus africanus*, which elicit a significant antimicrobial, preferably antifungal activity in vitro and in vivo, even under field and glasshouse conditions. Moreover, these extracts elicit a significant bio-stimulatory activity, expressed, above all, by an increased growth metabolism. Extracts or preparations from the aerial parts of the plants show a higher efficacy as compared to the soil parts of the plant. Furthermore, extracts or preparations from the combined aerial parts of the plants (flowers, leaves, stalks) show a higher antifungal and bio-stimulatory efficacy as compared to the sum of extracts or preparations from the single components of the aerial parts, indicating that synergism is participated in the involved biological processes. Furthermore, combined extracts or preparations from species of the genus *Agapanthus* and the species *Tulbaghia violacea* show a higher antifungal and bio-stimulatory efficacy as compared to the extracts or preparations of the single species and let assume the existence of a synergistic process.

The invention provides, in addition, compositions of combinations of extracts or preparations of different plant species. These combinations comprise preparations from species of the genus *Agapanthus*, preferably *A. africanus*, and other plant species, preferably garlic species, most preferably from *Tulbaghia violacea* (wild garlic). Alternatively, according to the invention, a preparation from species of the genus *Agapanthus* is combined with a preparation of a mixture of species of the Pink family and *Alfalfa* species, preferably in a specific ratio. In another embodiment of the invention provides combinations of species of the genus *Agapanthus* with *Tulbaghia violacea* and a mixture of species of the Pink family and *Alfalfa* species. These combinations elicit an increased and synergistic plant protective activity, preferably an antifungal and bio-stimulatory activity, as compared to the corresponding single-component preparations.

The invention provides finally at least four compounds isolated and purified from said extracts/preparations, which also show significant plant protecting activity, especially antifungal activity, when applied to other plants in vitro and in vivo, field cultivation included. These four compounds are: 3-[{O-β-D-glucopyranosyl-(1"-3')-α-L-rhamnosyl-(1"-2')}-β-D-glucopyranosyloxy]agapanthegenin, 5,7,4' tri-O-flavanone, 5,7,3',4'-tetra-O-acetylflavanone and trans-4,2',4'-tri-O-acetylchalcone.

The preparations according to the invention can be provided as crude extracts or as dried powder dependent on the process of their manufacture. The preparations may comprise additionally, especially for use in field cultivation, solid preferably pulverulent fillers or carrier materials according to the state of the art. Moreover, the preparations according to the invention may comprise conventional additives that augment or modulate the effect of the preparation.

The preparations according to the invention can be provided also in a liquid, preferably aqueous form, which can be uses as a spray, and thus can be easily atomized on the areas under cultivation. In such solutions or suspensions the extracts and preparations of the invention reveal their full plant protecting activity in a concentration range between 0.25 g (extract/powder)/l to 2 g/l, preferably from 0.5 g/l to 1 g/l. With respect to the antifungal activity of the preparations, the term "full plant protecting activity" means 100% inhibition of the mycelial growth of a typical fungal plant pathogen compared to a standard reference pesticide.

The invention also provides processes for the manufacture of the crude extracts and dry powder preparation based on extraction of the plants or plant parts with organic polar solvents, such as methanol or ethanol or mixtures thereof.

The invention finally provides a process of isolating, purifying and identifying substances from said extracts which show significant antifungal and bio-stimulatory activity in diseased plants in vitro and in vivo.

In more detail the invention provides:

A preparation suitable for biological plant protection based on plants or parts of plants from the genus *Agapanthus*, preferably the species *A. africanus*, in form of a crude extract, whereby said preparation is obtainable by the following process steps:
  (i) drying the plant material preferably at 30-40° C. preferably to the exclusion of sun light;
  (ii) grinding the dried plant material to a grit size between 0.2-2 mm;
  (iii) soaking the ground material in a polar organic solvent selected from the group consisting of methanol and ethanol, thus forming a suspension/solution
  (iv) performing a stirred extraction of the suspension and separating the supernatant from the solid phase;
  (v) repeating step (iii) and (iv) at least one additional time; preferably two times,
  (vi) combining the soluble organic phases of step (iv) and removing the organic solvent by preferably vacuum evaporation at 30-40° C., thus obtaining the crude extract residue.

Alternatively, a corresponding preparation in form of a dry powder, obtainable by the following steps:
  (i) drying the plant material at preferably 30-40° C., preferably to the exclusion of sun light;
  (ii) grinding the dried plant material to a grit size less than 0.1 mm, (iii) soaking the ground material in methanol or ethanol, preferably methanol, thus forming a suspension/solution;
(iv) performing a stirred extraction of the suspension;
(v) evaporating the solvent without prior separation of the solid phase from the soluble organic phase;
(vi) soaking the evaporated solid phase residue in ethanol or methanol, preferably ethanol and repeating steps (iv) and (v); and
(vii) drying the evaporated solid phase residue, thus obtaining a dry powder.

A corresponding preparation, wherein one or more of the different aerial parts (flowers, leaves, stalks) of the plants are used, preferably the flowers.

A corresponding preparation, wherein the combined aerial parts (flowers plus leaves plus stalks) are used; said preparation is showing an additional (synergistic) effect as compared to the over-all effect of the single components of the aerial parts of *Agapanthus*.

A corresponding preparation, wherein the soil plant parts are used.

A corresponding preparation comprising:
3-[{O-β-D-glucopyranosyl-(1"-3')-α-L-rhamnosyl-(1"-2')}-β-D-glucopyranosyloxy]agapanthegenin, and/or
5,7,4' tri-O-flavanone and/or 5,7,3',4'-tetra-O-acetylflavanone and/or trans-4,2',4'-tri-O-acetylchalcone.

A corresponding preparation comprising
3-[{O-β-D-glucopyranosyl-(1"-3')-α-L-rhamnosyl-(1"-2')}-β-D-glucopyranosyloxy]agapanthegenin, and 5,7,4' tri-O-flavanone, and 5,7,3',4'-tetra-O-acetylflavanone and trans-4,2',4'-tri-O-acetylchalcone.

A corresponding preparation, which further comprises solid, pulverulent carrier materials or fillers and/or additives that augment or regulate the effect of the preparation.

A corresponding preparation in form of an aqueous solution or suspension, which can be easily sprayed and distributed on fields and areas under cultivation, in which the plants to be protected are cultivated.

A corresponding, wherein the concentration of crude extract or the dry powder is in the range from 0.25 g/l to 2 g/l, preferably from 0.5 g/l to 1 g/l.

A composition comprising a first plant preparation as specified above and second plant preparation in form of a crude extract, dry powder or an aqueous suspension or solution thereof, wherein said second plant preparation exerts an additional or even synergistic plant protective effect on the plants or parts thereof treated with the composition.

A corresponding composition comprising as second plant preparation a preparation deriving from garlic species, preferably *Tulbaghia violacea*, whereby said second preparation is obtained by analogous process steps as said first preparation.

A corresponding composition comprising as second plant preparation a preparation deriving from a mixture of species of the Pink family and *Alfalfa* species, wherein preferably the proportion by weight of the dried Pink species material is between 80 and 99%, and said second plant preparation is obtained by analogous process steps as said first plant preparation.

A composition comprising (i) said first plant preparation, (ii) said second plant preparation, and (iii) a third plant preparation deriving from a mixture of species of the Pink family and *Alfalfa* species, wherein preferably the proportion by weight of the dried Pink species material is between 80 and 99%, whereby each preparation is in form of a crude extract, dry powder or an aqueous suspension or solution thereof, and said second and third plant preparation exert an additional plant protective effect on the plants or parts thereof treated with the composition.

The use of a preparation/composition as described above as a biological plant protective agent.

The use of a preparation/composition as described, wherein the biological plant protective agent is an antimicrobial agent, preferably an antifungal agent, which preferably inhibits or reduces the mycelial growth of fungi and is enabled to prevent plants, preferably crop, from infection by fungi under field conditions.

The use of a preparation/composition as described above as a bio-stimulatory agent, which exerts growth induction The use of a preparation/composition as described above as a bio-stimulatory agent, which induces systemic acquired resistance (SAR) in plants or plant parts treated with the agent.

The corresponding uses, wherein the applied *Agapanthus* preparations derive from the combined aerial parts of *Agapanthus*.

The corresponding use, wherein the activity or efficacy of said preparation is higher than the sum of the activities or efficacies of preparations based on the respective single components of the aerial parts of *Agapanthus*.

A process for the preparation of a crude extract or a dry powder preparation or aqueous suspensions or solutions thereof from *Agapanthu* as defined above, comprising the following steps:
(i) drying plant material from *Agapanthus* at 30-40° C., preferably to the exclusion of sun light;
(ii) grinding the dried plant material to a grit size between 0.1-3 mm, preferably between 0.2-2 mm;
(iii) soaking the ground material in a polar organic solvent, such as methanol or ethanol, preferably 90-10% methanol or ethanol or mixtures thereof, thus forming a suspension/solution;
(iv) performing a stirred extraction of the suspension and separating the supernatant from the solid phase;
(v) repeating step (iii) and (iv) at least one additional time; preferably two times,
(vi) combining the soluble organic phases of step (iv) and removing the organic solvent by preferably vacuum evaporation at 30-40° C., thus obtaining the crude extract residue;
and in the case of the preparation of an aqueous preparation;
(vii) suspending the resultant crude extract in water in a suitable concentration preferably in a range between 0.1 g/l and 2 g/l, more preferably between 0.5 g/l and 1 g/l.

A compound of formula I,

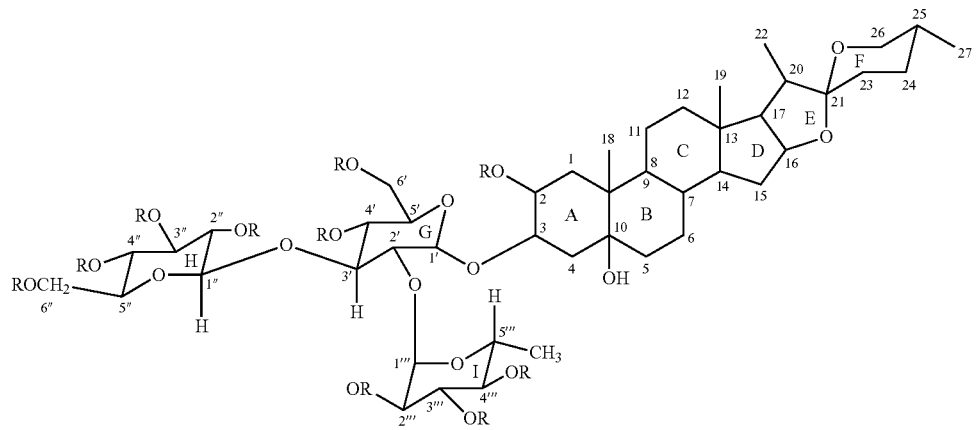

wherein R=H or acetyl.

A corresponding compound isolated from a preparation as described, wherein said compound is 3-[{O-β-D-glucopyranosyl-(1"-3')-α-L-rhamnosyl-(1"-2')}-β-D-glucopyranosyloxy]agapanthegenin.

A corresponding composition suitable for biological plant protection comprising a compound of formula I or, more specifically, 3-[{O-β-D-glucopyranosyl-(1"-3')-α-L-rhamnosyl-(1"-2')}-β-D-glucopyranosyloxy]agapanthegenin and at least one flavonoid compound selected from the group consisting of 5,7,4' tri-O-flavanone, 5,7,3',4'-tetra-β-acetylflavanone and trans-4,2',4'-tri-O-acetylchalcone.

The use of said isolated compounds as plant protective agent, wherein the plant protective agent is preferably an antifungal agent that inhibits the mycelial growth of fungi.

An alternative process for the preparation of a crude extract or a dry powder preparation or aqueous suspensions or solutions thereof derived from *Agapanthus* as defined above comprising the steps (ia) drying the plant material from *Agapanthus* at preferably 30-40° C., preferably to the exclusion of sun light;

(iia) grinding the dried plant material to a grit size less than 0.1 mm, (iiia) soaking the ground material in a first polar organic solvent, preferably 90-100% methanol, using 1.0-3.0 ml/g dry weight of the ground plant material, thus forming a suspension/solution;

(iva) performing a stirred extraction of the suspension;

(va) evaporating the solvent without prior separation of the solid phase from the soluble organic phase;

(via) soaking the evaporated solid phase residue in a second polar organic solvent, preferably 90-10% ethanol, using 1.0-3.0 ml/g dry weight of the ground plant material, and repeating steps (iva) and (va);

(viia) drying the evaporated solid phase residue, thus obtaining a dry powder; and in the case of the preparation of an aqueous preparation, (viii) suspending/solving the resultant dry powder in water in a suitable concentration, preferably in a range as indicated above.

DETAILED DESCRIPTION OF THE INVENTION (A) General Definitions

Above and below terms and expressions are used which have according to the understanding of the this invention the following meanings:

The term "plant protecting agent" or "plant protective agent" means, if not otherwise specified, any kind of synthetic or natural agent, product, extract, composition that is effective in a broad sense for the protection and health of a plant against infection and damages by pathogens in vitro and/or in vivo. The term includes agents, products, extracts, compositions or single isolated components of extracts which may show a couple of different biological activities and/or properties, such as antimicrobial, antiviral, antifungal, and biostimulatory activity/efficacy, growth inducing/promoting activity (with respect to the plant to be protected), growth inhibitory activity (with respect to the plant(s) competitive to the plant to be protected), systemic and/or immunological acquired resistance inducing/promoting activity, and allelopathy inducing/promoting activity.

The term "biological plant protection" means according to the invention, if not otherwise specified, that the protection of a plant is achieved by naturally occurring or naturally derived substances or sources preferably from plants, and not by synthetic or chemical means or agents, which do not occur in nature, preferably plants or part of plants.

The term "biological plant protecting (protective) agent" is thus, consequently a plant extract, a plant preparation, a composition based on plants or parts thereof, or an agent isolated from a plant extract/preparation/composition, which all show significant efficacy against a plant pathogen in vitro and/or in vivo. This term includes also chemically synthesized compounds which are structurally and functionally identical with the isolated naturally derived compound, but excludes expressively chemically synthesized pesticides and related compounds having no natural derived counterpart.

The term "pesticide" means according to the invention, if not otherwise specified, not naturally derived or occurring, synthetic compounds, agents or compositions which have plant protecting efficacy.

The term "plant pathogen" means a compound or composition or living material, such as a microorganism (including viruses), which causes disease or damage to the plant. In a narrower scope of the invention the term is focused to pathogenic microorganisms including metabolic products of these microorganisms.

The term "antimicrobial" according to the invention encompasses an efficacy or activity against microorganisms, including viruses, bacteria and fungi, that reduces or eliminates in vitro and/or in vivo the (relative) number of active microorganisms which attack the plant or parts thereof to be protected. Thus, the term includes the terms "antiviral", "antibacterial", and "antifungal". An "antimicrobial agent" according to the invention is a biological plant protecting agent as specified above, which prevents or reduces infections or damages of a plant caused by a pathogenic microorganism.

The term "antibacterial" means according to the invention an activity or efficacy (e.g. of an agent or extract, etc.), that reduces or eliminates the (relative) number of active bacteria. An "antibacterial agent" according to the invention is a biological plant protecting agent as specified above, which prevents or reduces in vitro and/or in vivo infections or damages of a plant caused by a pathogenic bacterium.

The term "antiviral" means according to the invention an activity or efficacy (e.g. of an agent or extract, etc.), that reduces or eliminates the (relative) number of active viruses. An "antiviral agent" according to the invention is a biological plant protecting agent as specified above, which prevents or reduces in vitro and/or in vivo infections or damages of a plant caused by a pathogenic virus.

The term "antifungal" means according to the invention an activity or efficacy (e.g. of an agent or extract, etc.), that reduces or eliminates the (relative) number of active fungi. An "antifungal agent" according to the invention is a biological plant protecting agent as specified above, which prevents or reduces in vitro and/or in vivo infections or damages of a plant caused by a pathogenic fungus. The antifungal activity may lead to the inhibition of mycelial growth as well as spore germination of fungi.

The term "bio-stimulatory" means according to the invention, if not otherwise specified, an activity or efficacy which stimulates, increases or improves many different processes in the plant or plant parts, such as improved generation of growth promoting substances like sugars and amino acids, improved adequate supply of cells with available nutrients and growth regulators, enhanced cell metabolism, improved cell decontamination, enhanced immune defense, promotion of growth and yield, induction of systemic acquired resistance (SAR), inhibition of growth and yield of competing plants (allelopathy). The bio-stimulatory activity can be caused by agents, plant extracts and compositions including metabolic compounds synthesized by the plant to be protected after induction of their synthesis by said bio-stimulatory agent. A "bio-stimulatory agent" according to the invention is a biological plant protecting agent as specified above, which shows the above-specified bio-stimulatory properties in a plant treated with this agent in vitro and/or in vivo.

A "plant growth regulator" is a compound or a mixture of substances either natural or synthetic, that modifies or controls one or more specific physiological processes within a plant. If the compound is produced within the plant it is called a plant hormone e.g. auxins, gibberellins, abscisic acid and ethylene.

"SAR" (Systemic Acquired Resistance) occurs in a plant or parts thereof according to the invention if it shows induction or enhancement of activity of defense or protection related enzymes (PR-proteins). Such enzymes include, for example, peroxidase, β-1,3-glucanse and NADPH oxidase.

(B) Plant Description

*Agapanthus* is originally indigenous to South Africa. Studies on its distribution indicated that the evergreen species of *Agapanthus* grows wildly from the south-western Cape eastwards into Natal and further North. It is also grown in Europe, America, Australia, New Zealand and South America.

The taxodermic classification of *Agapanthus africanus* is:
Division: Magnoliophyta
Class: Liliopsida
Subclass: Lilidae
Family: Amaryllidaceae
Subfamily: Lilidaceae
Genus: *Agapanthus*
Species: *Agapanthus africanus* (*A. umbelattus*)

The genus *Agapanthus* (L.) Hoffmg (Alliaceae) may be divided into two groups according to the type of flowers they bear namely those with flowers having short tubes with perianth segments spreading out widely, and those with long tubes and perianth segments that do not spread much. The genus is sometimes also divided into evergreen or deciduous types. *A. africanus* (synonym *A. umbellatus*) is the evergreen one with flowering stems of about 60 cm in length and deep blue flowers with a darker stripe down the center of each petal. It grows 30 to 60 cm in height and has shorter, fewer and more leathery leaves than the subspecies *A. praecox* (*orientalis*). It also has much fewer flowers, usually about 12 to 18, in a smaller head than that of *A. praecox* and flowers from December to March. There is also a rare white form, *A. walshii*.

*A. africanus* can be cultivated. It is a perennial with a large root system that enables it to go without water for long periods of time. As the root volume increases from season to season and give rise to new plants spontaneously, roots can also be used to multiply the plant as a cultivation practice. Eventually the plants begin to suffer through being overcrowded. For this reason the clumps which they form should be lifted every few years and divided. *A. africanus* grows in any kind of soil. To obtain good results in poor soil, it may be necessary to prepare trenches of approximately 30-45 cm deep and incorporate compost and manure. Although the plants are drought tolerant, they flower better if watered regularly during spring and summer when flower formation is at its peak.

(C) Microorganisms

Six common South African plant fungal pathogens are chosen to test for the fungitoxic properties of the plant extracts. These fungal pathogens included *Botrytis cinerea* Pers.:Fr. (Hyphomycetes), *Fusarium oxysporum* Schlechtend.:Fr. (Hyphomycetes), *Sclerotinia rollfsii* Sacc. (Agonomycetes), *Rhizoctonia solani* Kühn (Agonomycetes), *Botryosphaeria dothidea* (Moug.: Fr.) Ces. & De Not. (Loculoascomycetes) and *Pythium ultimum* Trow (Oömycetes). Plant pathogenic bacteria used in this study include *Agrobacterium tumefaciens* Smith and Townsend, *Clavibacter michiganense* Spieckermann pv. *michiganense* Smith, *Erwinia carotovora* pv. *carotovora* Jones, *Xanthomonas campestris* Pammel pv. *phaseoli* Smith, *Ralstonia solanacearum* Smith and a human bacterium *Moraxella catharrhalis*.

(D) Screening of Crude Extracts from *Agapanthus africanus* for In Vitro Antimicrobial and Biostimulatory Activity (1) General Crude extracts of different plant parts of *Agapanthus africanus* are screened in vitro against six plant pathogenic fungi, six plant pathogenic bacteria as well as one human bacterium (see below. The plant parts are dried, ground and extracted with preferably methanol as specified in more detail in the Examples.

In another approach preparations comprising extracts/dry powders from *Agapanthus africanus* in combination with respectively produced extracts from wild garlic (*Tulbaghia violacea*) are tested with respect to their plant protecting activities.

A standard chemical, Carbendazim/Difenoconazole is used as a positive control. Screening activities are performed using a disk diffusion method. To determine the bio-stimulatory activity of crude extracts, two methods are applied. Firstly, the effect of the extracts on the respiration rate of a monoculture yeast cells is measured using a specially manufactured respirometer. Secondly, radish seeds are used to ascertain the influence of crude extracts on seed germination as well as root and coleoptile growth in seedlings. In both techniques, ComCat® a commercial biostimulant (EP 1051075) is used as a positive control.

(2) Antimicrobial Properties of *A. africanus* Crude Extracts

Crude methanolic extracts of all different plant parts of *A. africanus* significantly (P<0.05) inhibit the mycelial growth of all test fungi, in vitro, at a concentration of 1 mg/ml (FIG. 1) compared to the standard fungicide, used as a positive control.

The root extract completely inhibits mycelial growth of *B. cinerea*, *S. rolfsii*, *R. solani* and *B. dothidea*, in vitro, and shows a degree of control against *F. oxysporum* (77%) and *P. ultimum* (64%). A crude leaf extract shows a similar inhibitory effect against *S. rolfsii*, *R. solani* (FIG. 1) and *B. dothidea*, slightly lower against *B. cinerea* (97%) and *F. oxysporum* (73%) but is equally effective against *P. ultimum* as was the root extracts (FIG. 1). Extracts from the stalk also completely inhibit mycelial growth of *S. rolfsii* and *B. dothidea* but are slightly less effective against *B. cinerea* (87%) and *F. oxysporum* (73%) (FIG. 1).

To sum up, a preliminary assessment of the inherent potential of crude extracts from *A. africanus*, based on in vitro results, indicates that *B. cinerea*, *S. rolfsii*, *R. solani* and *B. dothidea* are most sensitive to treatments with extracts from all plant parts. *P. ultimum*, and to a lesser extent *F. oxysporum*, are more resistant to treatment with the crude extracts (Table 1).

(3) Biostimulatory Properties of *A. africanus* Crude Extracts

Figure 2:
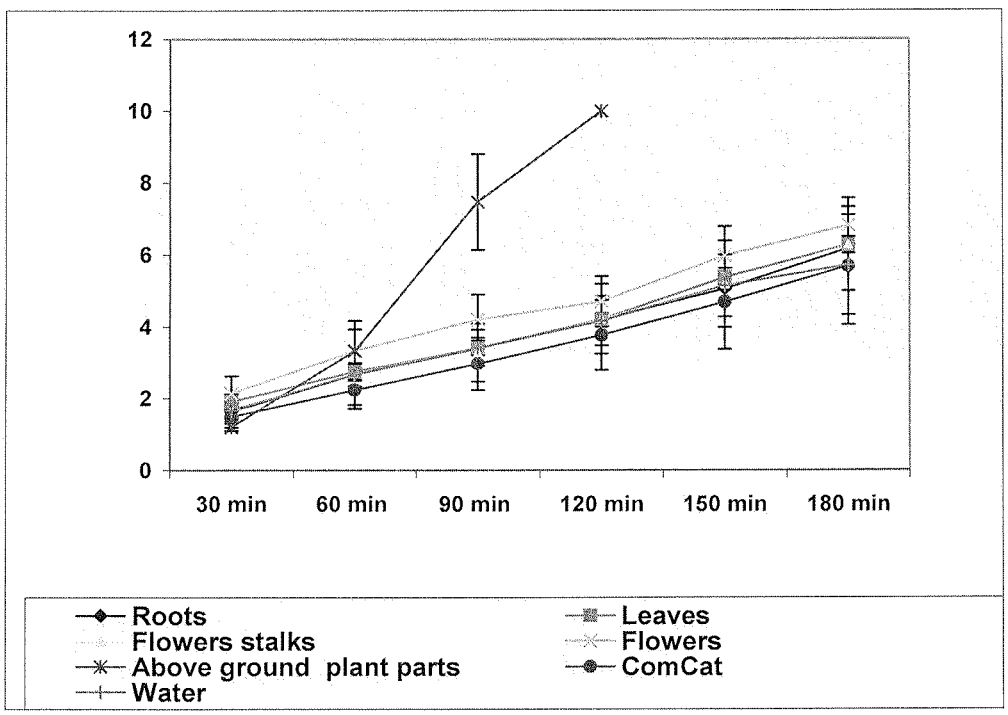

In order to establish whether crude extracts of *A. africanus* plant parts possess inherent biostimulatory properties, their effect on the respiration rate of a monoculture yeast cells are first determined in vitro over a three hour period. Compared to both a water and a positive control (ComCat®), similar respiration rates are observed when extracts of different plant parts are tested separately (FIG. 2). However, the aerial part crude extract increases the respiration rate of yeast cells significantly over the first two hours (FIG. 2).

Subsequently, the in vivo effect of crude extracts on the germination of radish seeds as well as seedling growth is determined. Crude extracts of the flowers, flower stalks, leaves and the aerial part crude extract significantly (P<0.05) increase seed germination by 21%, 18%, 16% and 6%, respectively, compared to the water control (Table 2).

Although most extracts seem to have a stimulatory effect on the germination of radish seeds in vitro, only the leaf and flower extracts show a significant stimulatory effect on root growth of the seedlings. Root, flower stalks and the aerial part crude extract, on the other hand, significantly inhibit root growth compared to the water control (Table 2).

TABLE 2

The effect of crude extracts from different plant parts of *A. africanus* on the germination of radish seeds as well as seedling growth

| Plant extracts | Germination (%)† | Root length (mm) | Coleoptiles length (mm) |
|---|---|---|---|
| Roots | 62.67 ± 10c | 30.62 ± 15.50d | 24.01 ± 7.69bc |
| Leaves | 71.33 ± 11.5ab | 43.14 ± 13.61a | 24.64 ± 4.12abc |
| Flowers stalks | 72.67 ± 5.78a | 38.40 ± 8.78bc | 26.40 ± 4.05ab |
| Flowers | 74.78 ± 5.96a | 43.09 ± 9.5a | 26.71 ± 3.07a |
| Aerial part | 65.22 ± 4.56bc | 35.81 ± 7.29c | 23.07 ± 2.37c |
| Comcat | 63.11 ± 3.45c | 40.31 ± 7.96ab | 22.12 ± 2.37c |
| Water (distil) | 61.67 ± 2.37c | 41.06 ± 7.46ab | 23.10 ± 2.33c |

†Values designated with different letters, within a column, indicate significant differences at the 5% level (P < 0.05) according to Duncan's multiple range procedure.

Both the flower stalk and flower extracts significantly increase coleoptile growth of radish seedlings in comparison to the water control. The commercial biostimulant, ComCat®, used as a positive control, has no significant effect on either seed germination or seedling growth.

TABLE 1

In vitro antifungal activity of crude extracts from different organs of *A. africanus*

| | | % Mycelial Growth Inhibition for different fungi | | | | | |
|---|---|---|---|---|---|---|---|
| Plant extract | Plant organ | *Botrytis cinerea* | *Fusarium oxysporum* | *Sclerotium rolfsii* | *Rhizoctonia solani* | *Botryosphaeria dothidea* | *Pythium ultimum* |
| Plant X | Root | 100a ± 0 | 75c ± 4 | 100a ± 0 | 100a ± 0 | 100a ± 0 | 63d ± 2 |
| | Leaves | 94ab ± 2 | 71c ± 2 | 100a ± 0 | 94ab ± 3 | 100a ± 0 | 64d ± 3 |
| | Stalks | 90b ± 3 | 74c ± 2 | 100a ± 0 | 99a ± 1 | 100a ± 0 | 63d ± 2 |
| | Flower | 98a ± 2 | 78c ± 5 | 100a ± 0 | 100a ± 0 | 100a ± 0 | 60d ± 4 |
| | *Standard | 100a ± 0 | 50e ± 2 | 51e ± 3 | 52e ± 2 | 67d ± 5 | 7f ± 2 |

The flower and the aerial part crude extracts also show almost the same inhibitory effect against all tested fungi, as it is the case for other crude extracts (FIG. 1). However, aerial part crude extracts are more effective in inhibiting the mycelial growth of *P. ultimum* (79%) than other plant part extracts when tested separately (FIG. 1). In all cases the crude extracts out perform the standard fungicide. However, none of the extracts exhibit antibacterial activity against any of the plant pathogenic bacteria tested.

(4) Antifungal Properties of *A. africanus* Crude Extracts Combined with Extracts from *Tulbaghia violacea*

A crude extract or a dry powder of wild garlic (*T. violacea*) is prepared analogously to the methods described here for species of the genus *Agapanthus*. The extracts or dried powders are mixed in a 1:1 ratio and aquous solutions are applied in different concentrations varying from 0.25 mg/ml to 2 mg/ml.

It is interesting to note that a 50:50 mixture of the two extracts, applied at 0.5 mg/ml, shows total control of the six test fungi (Table 3), whereas in comparison hitherto, applying separately the two-fold concentration (1 mg/ml) of the *A. africanus* preparation or the *T. violacea* preparation, inhibition of the mycelial growth of the test fungi is not complete. Even a concentration of 0.25 mg/ml of a combined extract/dry powder preparation (1:1) leads to an over-all inhibition of the same fungus system of more than 90%, indicating that significant synergism is effective in the combination system. The same effect is observable with other plant-protecting agents.

germination percentage of radish seeds indicating a stimulatory effect. It is possible that one or more active substance contained in the crude extracts could have had a stimulatory effect on one or more of the respiratory enzymes, most probably regulatory enzymes, or even storage material mobilization. Combined extracts/dry powders based on preparations from two or more plants having plant protecting properties, wherein at least one is a species of the genus *Agapanthus*, show over a broad range antifungal and bio-stimulatory efficacy at least in vitro based on synergistic effects.

TABLE 3

In vitro antifungal activity of crude extracts from the above ground parts of *A. africanus* (X) and *T. violacea* (Y) used together in a 1:1 ratio and applied at 0.5 mg/ml.

| Extract Mix (50:50) | Plant material | % Mycelial Growth Inhibition for different fungi Fungus | | | | | |
| --- | --- | --- | --- | --- | --- | --- | --- |
| | | *Botrytis cinerea* | *Fusarium oxysporum* | *Sclerotium rolfsii* | *Rhizoctonia solani* | *Botryosphaeria dothidea* | *Pythium ultimum* |
| Plant X + Plant Y (50:50) | Above ground parts | 100a ± 0 | 100a ± 0 | 100a ± 0 | 100a ± 0 | 100a ± 0 | 100a ± 2 |
| | Standard | 100a ± 0 | 70c ± 3 | 68c ± 4 | 38 ± 2 | 87bc ± 3 | 4f ± 1 |

Standard broad spectrum fungicide; Carbendazim/difenoconazole (Eria@)

Different letters following values indicate statistical significant differences.

(5) Summary Results

Results indicate that none of the plant extracts from *A. africanus* shows any antibacterial activity. However, crude extracts or dry powders of all different plant parts of *A. africanus* significantly (P<0.05) inhibit mycelial growth as well as spore germination in all test fungi, indicating a strong antifungal activity of the preparations according to the invention. Root and flower extracts as well as an extract of the aerial part crude extracts show significantly higher antifungal activity than extracts from leaves and stalks. Among the tested fungi, *Pythium ultimum*, and to a lesser extent *Fusarium oxysporum*, shows a degree of tolerance towards all extracts. This is especially significant in light of the experience that mycelial growth inhibition by fungicides is more difficult to accomplish than inhibition of spore germination. The average inhibitory effect of the plant extracts against the test fungi ranges between 59 and 100%. Of these the aerial part crude extract (leaves, stalks and flowers combined) is highest (92%), emphasizing the broad-spectrum fungicidal potential of the extract. Moreover, the potent anti-fungal activity shown by this combined extract indicate a synergistic effect of different active substances and support the assumption of differential accumulation of bioactive compounds in different organs of plants. An extract from the aerial part crude extract of *A. africanus* as well as a flower extract significantly enhances the respiration rate of a monoculture yeast cells and all plant part extracts enhance the germination of radish seeds, thus indicating that a bio-stimulatory in vitro activity is effective. The aerial part crude extract increases the respiration rate of a monoculture yeast cell substantially compared to the separate plant part extracts as well as to both the water control and the positive control, ComCat®. The same effect is not observed when the different plant part extracts were tested separately. All the crude extracts of different plant parts of *A. africanus* as well as the aerial part crude extract increased the (E) In Vivo Antimicrobial and Bio-Stimulatory Effects of Preparations from *Agapanthus*

(1) General

*Mycosphaerella pinodes* (Berk & Blox.) Vesterger., is a major constraint to field pea (*Pisum sativum* L.) production and is the most destructive and widespread disease throughout the field pea growing areas of the world. All aerial parts of the pea plant are susceptible to infection while growth, yield and seed quality are all adversely affected. The fungus infects pea seedlings as they emerge causing girdling stem lesions that reduce field pea populations and increase lodging. Later it also causes necrotic lesions on leaflets and stipules and, in exceptional circumstances, abscission of the leaflets. *M. pinodes* is spread via pycnideospores throughout the season. After germination of spores, the fungus grows over the plant surface for some distance before forming an apersorium and penetrating the cuticle. Symptoms are characterized by brown to purplish, coalescing lesions on aerial tissue. Crude extracts of flowers, roots, leaves and the aerial plant parts are subsequently tested under greenhouse conditions against *Mycosphaerella pinodes*, the cause of black spot or *Ascochyta* blight in peas. Fourth internode leaves are removed from four week old pea plants, placed on moist filter paper in petri dishes and inoculated with a *M. pinodes* spore suspension 30 min before and after treatment with the extracts. The control of *Ascochyta* blight by different concentrations of the crude extracts from different plant parts of *A. africanus* is measured in terms of lesion size over a 6 day period at 20° C. in a growth cabinet.

(2) In Vivo Antifungal Activity of Preparations of *Agapanthum* Under Glasshouse Conditions In the in vivo screening antifungal trial, using pea leaves inoculated with *M. pinodes* spores either before or after treatment with the plant extracts, the extract of *A. africanus* inhibits completely spore germination of *M. pinodes* at a concentration near 1 mg/ml, when the extract is applied before spore inoculation. This indicates that application of *A. africanus* on crops as a preventative measure has potential in the agricultural industry.

TABLE 4

In vivo antifungal activity of crude extracts from the above ground parts of *A. africanus* against *Mycosphaerella pinodes* on pea leaves

| Treatment | Extract concentration | Mean lesion size (mm) | % Inhibition |
|---|---|---|---|
| Extract sprayed on leaves first and spore inoculation followed 30 min later | 2 mg ml$^{-1}$ | 0 | 100% |
| | 1 mg ml$^{-1}$ | 0 | 100% |
| | 0.5 mg ml$^{-1}$ | 2.37 | 81% |
| | 0.25 mg ml$^{-1}$ | 4.07 | 68% |
| | *Fungicide standard | 0 | 100% |
| | Spores only | 12.8 | — |
| Leaves inoculated with spores first and extracts sprayed on leaves 30 min later | 2 mg ml$^{-1}$ | 0 | 100% |
| | 1 mg ml$^{-1}$ | 0.26 | 98% |
| | 0.5 mg ml$^{-1}$ | 3.8 | 70% |
| | 0.25 mg ml$^{-1}$ | 5.29 | 59% |
| | *Fungicide standard | 0 | 100% |
| | Spores only | 12.8 | — |

*Standard broad spectrum fungicide; Carbendazim/difenoconazole (Eria ©)

Treatment of detached pea leaves with crude extracts of different plant parts of *A. africanus*, both before and after inoculation with *M. pinodes* spores, results in significant differences among extracts, extract concentration and method of inoculation in suppressing lesion development (Table 4). Among extracts the aerial plant part extract is most effective in suppressing lesion development, caused by *M. pinodes* on detached pea leaves, especially when applied before spore inoculation. The aerial plant part extract is also effective at the lowest concentration (MIC=0.5 mg/ml) compared to other extracts. When this extract is applied after spore inoculation, suppression of lesion development on pea leaves is also statistically significant compared to other extracts although complete suppression is observed only with the highest concentration of 2 mg/ml (Table 4)

In comparison the flower extract performs second best in terms of lesion development suppression both when applied before or after inoculation (MIC between 1 and 2 mg/ml) The root extract completely inhibits lesion development only at a concentration of 2 mg/ml when applied before inoculation. Although complete suppression of lesion development is not observed with the 2 mg/ml concentration when the root extract is applied after spore inoculation, the degree of suppression is statistically significant compared to the untreated control, except at 0.25 mg/ml (Table 4). The leaf extract fails to suppress lesion development completely both when applied before and after spore inoculation but, in both cases, the degree of suppression obtained is significant compared to the untreated control, except at 0.25 mg/mg (Table 4).

Crude extracts of different plant parts of *A. africanus* suppress in vivo lesion development on detached pea leaves to variable degrees depending on the concentration applied as well as the time of inoculation. Of these the aerial part crude extract is most effective at all concentration levels tested, compared to the other plant part extracts, both when applied before and after inoculation of detached pea leaves with *M. pinodes* spores. The flower extract also shows significant suppression of lesion development at a relative low concentration. As the aerial plant part extract contains compounds from flowers, flower stalks and leaves, the possibility of different active substances contained in the different parts showing a synergistic effect in either inhibiting spore germination or mycelial infection or both is not excluded.

The ability of the aerial plant extract as well as the flower extract to completely suppress lesion development even when applied after inoculation of detached pea leaves, is especially significant considering that the standard fungicide failed to do so.

Treatment of detached pea leaves with root and leaf extracts is less effective in preventing *M. pinodes* infection at lower concentrations when applied both before and after spore inoculation compared to the aerial plant part and flower extracts. The necrotic lesions measured on pea leaves treated with root and leaf extracts at concentrations lower than 1.0 mg/ml are similar to that measured on control leaves inoculated with spores only. However, when applied to detached pea leaves before spore inoculation, both extracts still show significant suppression of lesion development. Interestingly, the aerial plant part extract, of which leaves formed the largest portion, performs best overall. A possible synergistic effect between compounds contained in flowers, flower stalks and leaves in enhancing the fungicidal properties of *A. africanus* again is assumed. In terms of the potential to develop a natural product from *A. africanus*, the fact that the root extract is less effective than the aerial plant part extract underlines its exclusion and implies non-destructive collection.

The present study confirms that, especially a combined crude extract of aerial plant parts of *A. africanus* at a concentration of 0.5 mg/ml and lower, has the potential to be applied as both a preventative or corrective measure against infection of pea plants by *M. pinodes* spores. There are strong indications that the extract possesses significant potential as a corrective broad spectrum antifungal agent. In conclusion, the efficacy of different plant part extracts of *A. africanus* varies in suppressing lesion development on detached pea leaves caused by *M. pinodes* in vivo. The aerial plant part extract is most effective, especially when applied before spore inoculation and at a relatively low concentration of 0.5 mg/ml. However, application at higher concentrations after inoculation with *M. pinodes* spores shows complete inhibition of spore germination or infection or both. Importantly, none of the extracts causes phytotoxic yellowing or necrosis on detached pea leaves even at the highest concentrations applied.

(3) Phytotoxic Effects of Preparations from *Agapanthus* on Pea Leaves Under Glasshouse Conditions The in vivo phytotoxicity rating of the aerial plant parts, flower, root and leaf crude extracts of *A. africanus*, in terms of its interaction with and potential to induce necrosis in pea leaves, reveals that the crude extract is not phytotoxic even at the highest concentration tested (Table 5a, b) and the symptomless effect of the extract is similar to that of the water and standard fungicide controls. All plant part extracts of *A. africanus* as well as the standard fungicide control differs significantly from the leaf necrosis induced by the *M. pinodes* spore suspension.

TABLE 5a

Mean foliar phytotoxicity symptom rating on a six-category scale following direct inoculation of fourth node pea leaflets with the highest concentration of crude aerial plant part, flower roots and leaf of *A. africanus*. Mean foliar phytotoxicity symptom

| Plant extracts applied as foliar treatments | Concentration at 2 mg/ml |
|---|---|
| Aerial plant parts | 0.0b |
| Flowers | 0.0b |
| Roots | 0.0b |
| Leaves | 0.0b |
| Standard fungicide | 0.0b |
| Spore suspension | 4.2 ± 0.8a |

TABLE 5b

Phytotoxic effect of crude extracts from *A. africanus* plants on pea leaves.

| Treatment | Extract Concentration | Mean Lesion size (mm) indicating phytotoxicity |
|---|---|---|
| Crude extract only | 2 mg ml$^{-1}$ | 0 |
|  | 1 mg ml$^{-1}$ | 0 |
|  | 0.5 mg ml$^{-1}$ | 0 |
|  | 0.25 mg ml$^{-1}$ | 0 |

None of the different plant part extracts of *A. africanus* show any phytotoxic effect on detached pea leaves even at the highest concentration applied.

(4) Control of *Sorghum* Covered and Loose Smuts by an Aerial Part Crude Extract of *Agapanthus africanus* Under Field Conditions Sorghum (*Sorghum bicolor* L. Moench) is an important source of food in many non-developed countries and serves as staple food for the majority of people. It is predominantly grown in small-scale production systems under a wide range of environmental conditions. However, production of sorghum is less than 1.0 ton/ha due to various reasons. Sorghum covered kernel (*Sporisorium sorghi* Link, G. P. Clinton) and loose kernel smuts (*Sporisorium cruenta* Kuhn, A. A. Potter) are major factors that account for low yields. Both diseases occur frequently where sorghum is grown without treating seeds against these two pathogens.

Treatment of sorghum seeds with an aerial part crude extract of *A. africanus* before planting completely (100%) ($P<0.05$) reduce the incidence of both covered smut (Table 6a) and loose smut (Table 6b) compared to the corresponding untreated controls, and in both cases compared favourably with the synthetic fungicide Thiram.

TABLE 6a

Effect of an aerial part crude extract of *A. africanus* on the percentage covered kernel smut disease incidence under field conditions.

| Treatments | Mean plant population | % mean smut incidence | Yield (ton ha$^{-1}$) |
|---|---|---|---|
| Aerial plant extract | 171 ± ?a | 0b | 3.0a |
| Thiram | 175a | 0b | 2.6ab |
| Control | 173a | 5a | 1.6b |

TABLE 6b

Effect of an aerial part crude extract of *A. africanus* on the percentage loose kernel smut disease incidence under field conditions.

| Treatments | Mean plant population | % mean smut incidence | Yield (ton ha$^{-1}$) |
|---|---|---|---|
| Aerial plant extract | 175 ± ?a | 0b | 2.9a |
| Thiram | 175a | 0b | 2.1ab |
| Control | 175a | 18a | 1.3b |

Values designated with different letters differed significantly ($P<0.05$) according to Duncan's Least Significant Difference (LSD) statistical procedure.

Inoculation of pre-planted sorghum seed with covered or loose smuts spores, without also treating the seeds with either Thiram or the crude *A. africanus* extract (untreated controls), significantly decreases the final yields (Tables 6a, b). In the case of covered smut the yield loss is 46.7% and, in the case of loose smut, 55.2%. However, in both cases, there is no significant difference in yield between plots treated with either Thiram or the *A. africanus* crude extract. Probably due to the high standard deviation, no significant difference in yield between the Thiram treated and untreated controls can be observed in both cases.

The percent covered and loose smuts incidences are negatively correlated ($R^2=-0.92$ and $-75$ respectively) with sorghum grain yield indicating the negative impact both smut diseases had on the yield.

(5) The Effect of *A. africanus* Extracts on the Defense Mechanism of Plants (SAR)

Figure 4:
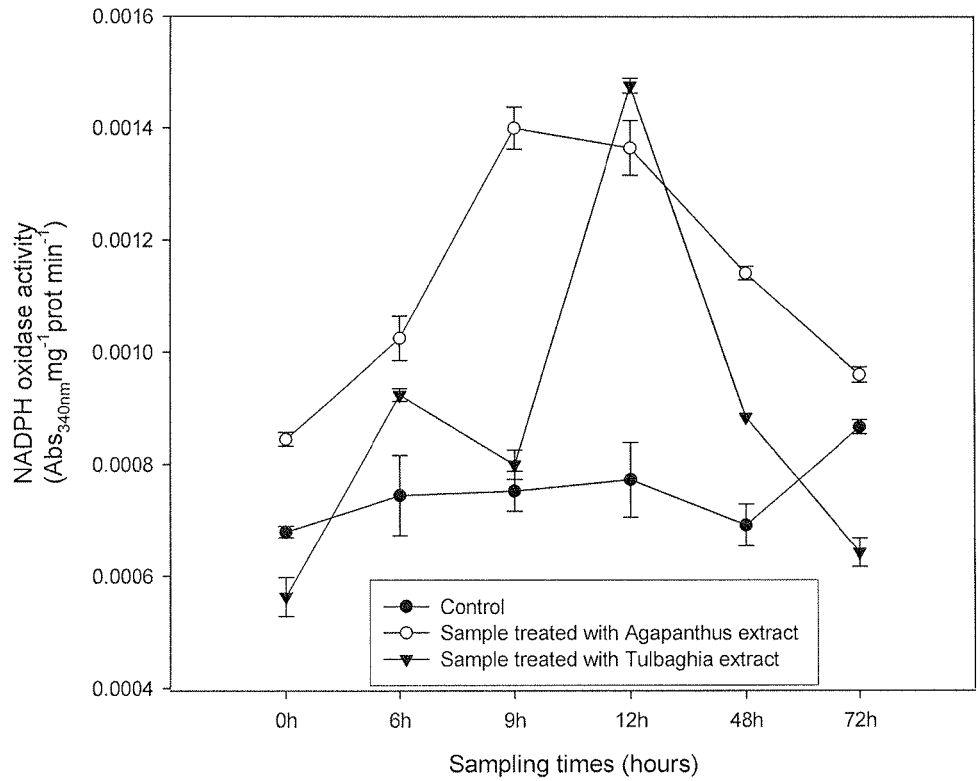
Figure 5:
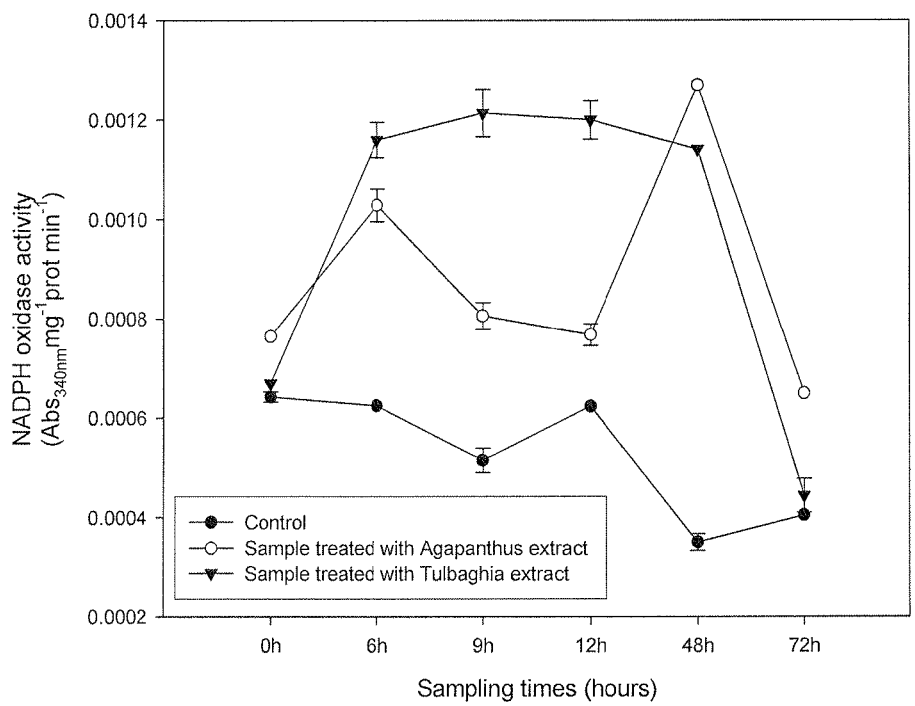
Figure 6:
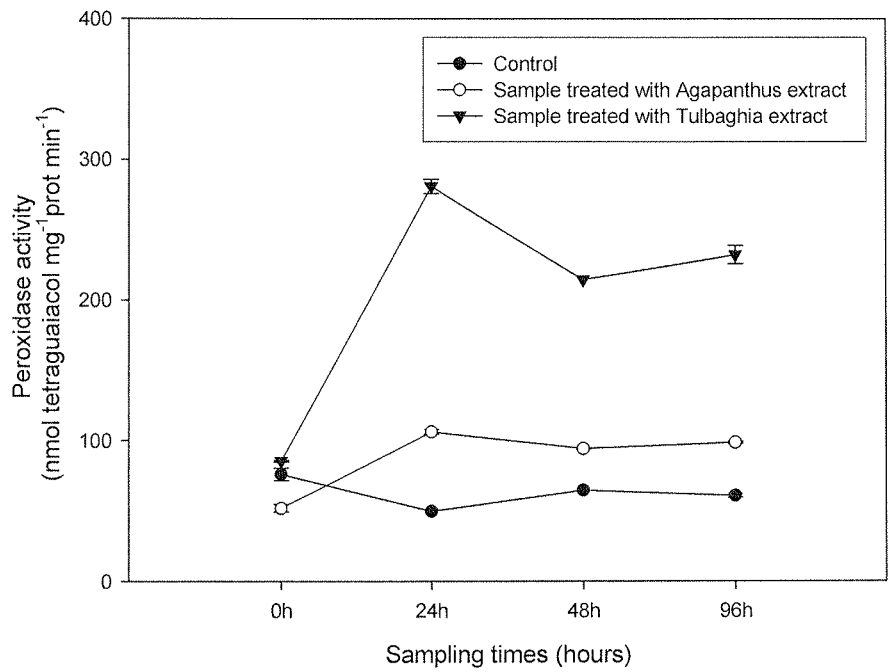
Figure 7:
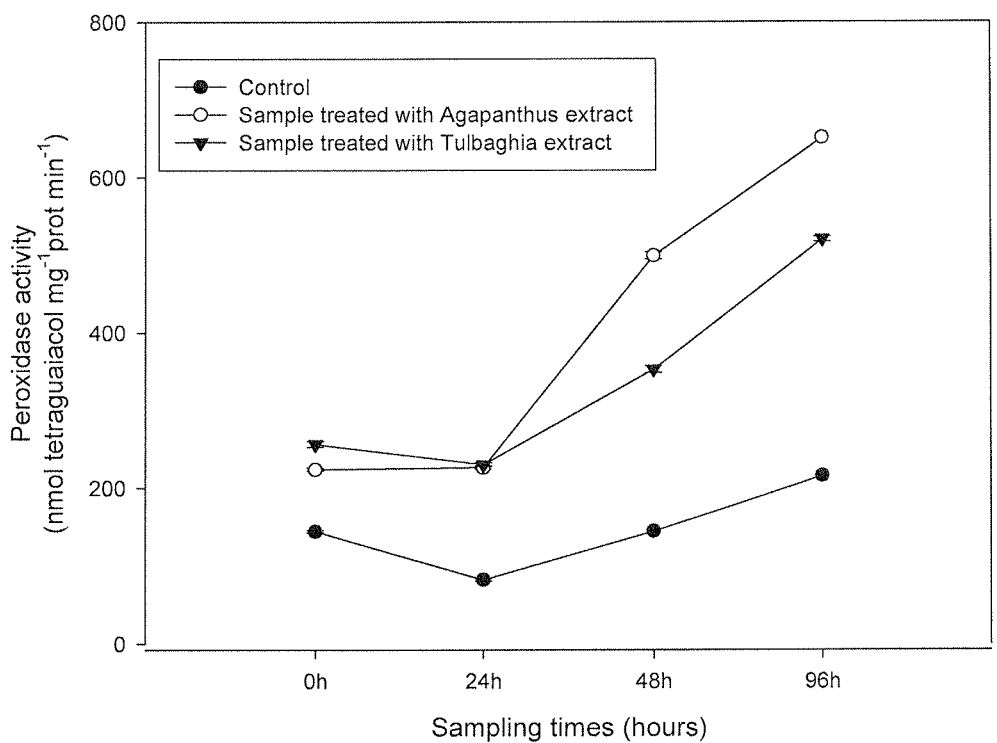

Plants (e.g. wheat and sunflower) elicit, when treated with an extract of *A. africanus* and another reference plant (*Tulbaghia violacea*) according to the invention, a significant activation of PR-proteins such as NADPH oxidase, peroxidase and β-1,3-glucanse. Wheat plants treated with the *A. africanus* extract show strong induction in NADPH oxidase activity after 6 h reaching the highest activity at 9 h (112%) over the previous sampling time. Activity remained high for up to 48 h (FIG. 4). Sunflower reacts to treatment with the *A. africanus* extract in the sense that two peaks in NADPH oxidase activity can be observed. The first peak is reached 6 h after treatment with an increase in activity of 61% over the previous sampling time while the second peak in activity is reached 48 h after treatment with an increase in activity of 333% over the previous sampling time (FIG. 5). From these results it seems that in the C4 plant, wheat, activity induction by treatment with the *A. africanus* extract is more pronounced than in sunflower, a C3 plant. Wheat treated with the *A. africanus* extract shows a significant induction (100%) in peroxidase activity 24 h after treatment and this activity is maintained over the test period (FIG. 6). In the case of sunflower the *A. africanus* extract induces peroxidase activity significantly especially after 48 h and 96 h (FIG. 7). For *A. africanus* the induction is 212% after 48 h and 230% after 96 h. The sunflower control, however, shows a slight increase in peroxidase activity over the 96 h period indicating some natural resistance. *Agapanthus* extracts induce defence mechanisms in wheat and sunflower plants. These extracts induce localized acquired resistance, the accumulation of PR-proteins by gene activation and ultimately systematic acquired resistance. The fact that the extracts induce a defense response in both the wheat and sunflower samples indicate that the extracts are responsible for the induction of a general broad-spectrum defense response. The extract-induced increase in defense related enzyme activities was lower, but comparable to the increase obtained during infection with resistant cultivars (F) Isolation, Purification and Identification of Antifungal Compounds from Root and Aerial Plant Part Extracts of *Agapanthus africanus*

(1) General

Although information about the chemical analysis of different plant parts of *A. africanus* is scanty, initial attempts was made by Takeda et al. (1955, *Chemistry Abstract* 50) who isolated and identified the compound yuccagenin from the roots. Others (Stephen, 1956 *Journal Chemistry Society* 1167; Mathew et al., 1957 *Journal Chemistry Society* 262), working with several unspecified species of *Agapanthus*, reported the new spirostan sapogenin, agapanthagenin Subsequently, in addition to the previously reported compounds, Gonzalez et al. (1973 *Phytochemistry* 13:627-631) isolated and identified two new spirostan sapogenins from the root system of *A. africanus*. Most previous studies concentrated on the isolation and identification of natural compounds from the root parts of *A. africanus*, but the relationship between these compounds and antimicrobial activity has not been established. Moreover, virtually nothing is known about the chemical composition of the aerial plant parts as well as their fungicidal properties.

(2) Antimicrobial Activity of Liquid-Solid Extractions of the Roots and Aerial Plant Parts The semi-purified fractions of different plant parts of *A. africanus*, obtained by means of liquid-solid extraction, differ significantly in inhibiting the mycelial growth of *F. oxysporum* (Table 8). The semi-purified extract of the roots, contained in diethyl ether, and both the ethyl acetate and dichloromethane extract of the aerial plant parts, significantly ($P<0.05$) inhibit mycelial growth of *F. oxysporum* compared to the hexane extract (Table 8). The diethyl ether root fraction showed the highest inhibition (62%) compared to the ethyl acetate and dichloromethane fractions that showed similar inhibition effects (51%).

In case of the combined aerial plant part extract, both the ethyl acetate and dichloromethane semi-purified liquid-solid extracts are most active and completely inhibit the mycelial growth of *F. oxysporum* (Table 7). This is statistically significant compared to the antifungal activity of both the hexane and diethyl ether fractions and compared favorably with the standard fungicide, Carbendazim/difenoconazole. Mycelial growth inhibition of *F. oxysporum* by semi-purified fractions of the aerial plant parts is also significantly ($P<0.05$) higher than that of the roots (Table 7).

TABLE 7

Antifungal activity of semi-purified liquid-solid extractions of the roots and aerial parts of *A. africanus* against *Fusarium oxysporum*

| | Mycelial growth inhibition (%)† Plant part | |
|---|---|---|
| Solvent | Roots | Aerial parts |
| Hexane | 24.3d | 5.4c |
| Diethyl ether | 62.3b | 13.7b |
| Ethyl acetate | 51.1c | 100a |
| Dichloromethane | 51.3c | 100a |
| Fungicide | 100a | 100a |

†Values designated with different letters within a column indicate a statistically significant difference at the 5% level ($P < 0.05$) according to Duncan's multiple range procedure.

The recovered yields of the root and aerial plant part liquid-solid extractions are presented in Table 8. Despite its low activity, the hexane solvent system provides high amounts of semi-purified residue of the roots and aerial plant parts ranging between ca. 4.3 to 5.4% while the diethyl ether solvent system provides ca. 3% and 2% from the roots and aerial plant parts, respectively. The ethyl acetate solvent system yields approximately ca. 1% residues in both the root and aerial part extracts while the recovered yield from the dichloromethane solvent system is less than ca. 1% in both cases.

TABLE 8

Residual yield recovered from *A. africanus* root and aerial plant part extracts obtained by means of liquid-solid extraction with a series of solvents, after drying at 35° C. The original dry mass of crude extracts is indicated in brackets.

| Solvents | Crude root extract (268.5 g) | Crude aerial part extract (368.83 g) |
|---|---|---|
| Hexane | 14.5 g | 15.89 g |
| Diethyl ether | 7.6 g | 5.96 g |

TABLE 8-continued

Residual yield recovered from *A. africanus* root and aerial plant part extracts obtained by means of liquid-solid extraction with a series of solvents, after drying at 35° C. The original dry mass of crude extracts is indicated in brackets.

| Solvents | Crude root extract (268.5 g) | Crude aerial part extract (368.83 g) |
|---|---|---|
| Ethyl acetate | 3.09 g | 4.33 g |
| Dichloromethane | 0.36 g | 0.45 g |

The diethyl ether extract of the root and the ethyl acetate as well as the dichloromethane fractions of the aerial parts show the highest (>50%) antifungal activity against *F. oxysporum*. However, as the recovery of compounds in the dicholoromethane fraction is extremely low (Table 8), only the ethyl acetate fraction of the aerial parts, together with the diethyl ether fraction of the roots, are chosen for further activity directed column chromatography fractionation.

(3) Activity Directed Column Chromatography Fractionation of the Most Active Liquid-Solid Extracts After collecting 300 column chromatography fractions of the diethyl ether root extract, every third fraction is spotted on a Q-TLC plate and developed with butanol:acetone:methanol (7:2:1; v/v) in order to obtain TLC profiles used as an indicator for combining fractions with similar profiles. In this way 17 combined column fractions can be obtained from the root extract of which nine showed high mycelial growth inhibition (65-97%) against *F. oxysporum* (Table 9). After treating the ethyl acetate aerial part fraction in the same way, 20 combined column chromatography fractions are obtained of which six were active in inhibiting the mycelial growth of *F. oxysporum* by more than 50% (Table 9).

Although nine of the combined column chromatography root fractions show high mycelial growth inhibition against *F. oxysporum* at a relatively low concentration of 625 µg/ml (w/v), only fraction 13 is used for further purification by means of preparative thin layer chromatography (PTLC) due to the extremely low recovery of the other fractions. In the case of the aerial plant parts, only column fraction 14, that showed complete mycelial growth inhibition against the test organism at the low concentration of 125 µg/ml (w/v), was further purified (Table 9).

TABLE 9

Antifungal activity of combined fractions obtained from the most active root and aerial plant part liquid-solid extracts following column chromatography against *F. oxysporum*. Only the most active combined column chromatography fractions are shown.

| Plant part | Combined column fraction number | % mycelial growth inhibition of *F. oxysporum* |
|---|---|---|
| Roots | 8 | 76 |
| | 9 | 67 |
| | 10 | 93 |
| | 11 | 97 |
| | 12 | 83 |
| | 13 | 83 |
| | 14 | 74 |
| | 16 | 65 |
| | 17 | 71 |
| Aerial plant parts | 7 | 58 |
| | 8 | 60 |
| | 14 | 100 |
| | 17 | 57 |
| | 18 | 55 |
| | 19 | 53 |

(4) Preparative Thin Layer Chromatographic (PTLC) Purification of Active Compounds from Column Chromatography Fractions Following preparative thin layer chromatography purification of active column fraction number 13 obtained from the root, 12 purified P-TLC fractions can be recovered, of which fraction 9 is most active (95%) against *F. oxysporum* (Table 10). In the case of active column fraction number 14 obtained from the aerial parts, three purified P-TLC fractions are recovered following washing with acetone, of which fraction number 1 shows complete mycelial growth inhibition against *F. oxysporum* (Table 10).

TABLE 10

Antifungal activity of P-TLC fractions obtained from root and aerial plant parts against *F. oxysporum*.

| P-TLC fractions | Mycelial growth inhibition (%) against *F. oxysporum* |
|---|---|
| Fraction 9 of the root | 95 |
| Fraction 1 of the aerial plant parts | 100 |

After controlling the most active P-TLC fractions of both the root and aerial parts for purity, by obtaining Q-TLC profiles after acetylating the molecules and acidifying the mobile phase with 1N HCl, the root fraction consists of four compounds (Table 11). By means of acidified P-TLC separation, these four compounds are purified and tested for antifungal activity. All four compounds are highly active. The active P-TLC fraction of the aerial parts proves to contain only one pure compound that is active (Table 11). All five of these pure compounds are subsequently subjected to nuclear magnetic resonance (NMR) spectroscopy in order to elucidate their molecular structures.

TABLE 11

Antifungal activity of pure compounds obtained from the most active P-TLC root and aerial plant part fractions, following acidification, against *F. oxysporum*.

| Plant part | Compound number | % mycelial growth inhibition of *F. oxysporum* |
|---|---|---|
| Roots | 1 | 100 |
|  | 7 | 87 |
|  | 8 | 93 |
|  | 9 | 97 |
| Aerial plant parts | 1 | 100 |

(5) Identification of Active Compounds Purified from Roots and Aerial Parts of *A. africanus* by Means of Nuclear Magnetic Resonance (NMR) spectroscopy Based on the $^1$H NMR spectra the single antifungal substance derived from the combined aerial plant parts of *A. africanus* provides a novel compound, saponin (1). Exactly the same saponin (1) can be identified as one of the four active substances derived from the roots of *A. africanus* together with three known flavonoids, 5,7,4'-trihydroxyflavanone (7), 5,7,3'4'-tetra-O-acetylflavanone (8) and trans-4,2',4'-Tri-O-acetylchalcone (9). Structural elucidation can be achieved via spectroscopic methods (1D NMR and 2D NMR) FAB and EI-MS spectrometry, and chemical methods such as hydrolysis.

(6) Saponin (1) Isolated from Both the Roots and Aerial Parts of *A. africanus*

The methanol extract from the roots and aerial plant parts of *A. africanus* yields compound (I) as a light brown precipitate in relatively large amounts. To obtain an acceptable level of purity, the fractions are washed repeatedly with acetone. This, and the highly insoluble nature of compound (I) (FIG. 3A), invariably lead to substantial losses, prohibiting reliable quantification. Due to the complexity of the $^1$H NMR spectrum of the non-derivatised saponin, the peracetate derivative (2) (FIG. 3B) is used in the structural elucidation. FAB-MS shows the [M+H]$^+$ ion at m/z 448, consistent with the molecular formula $C_{27}H_{44}O_5$ of the aglycone with the molecular mass of 448.

(7) Isolation and Identification of Flavones

In addition, flavanones (compound 7) and (compound 8) can be isolated from the roots after acetylation of fractions nine of the diethyl ether extract by means of P-TLC chromatography. Characteristic of these compounds is the presence of the 3-CH$_2$ [(two doublets of doublets, δ (3.00-3.15) and (2.70-2.85)] and the 2-H [(doublets of doublets, δ (5.00-6.00)] in their $^1$H NMR spectra.

Besides the sapogenin compound isolated from the root parts of *A. africanus*, by far the most frequently encountered flavanone, naringenin (5,7,4'-trihydroxyflavanone), was identified

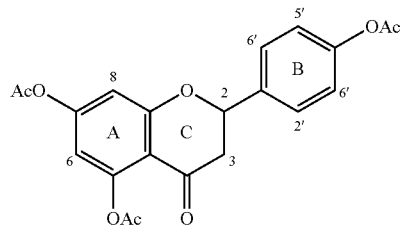

It is common as a free phenol, occurs with a wide variety of glycosylation patterns, has been isolated in all of its possible O-methylated forms and is susceptible to various C-alkylation processes (Batterham et al., 1964). Naringenin can be isolated after acetylation and P-TLC separation as the 5,7,4'-tri-O-acetyl derivative (7).

Additionally, 5,7,3'4'-tetra-O-acetylflavanone (8) can be isolated after acetylation and PLC separation from fraction number nine of the root part.

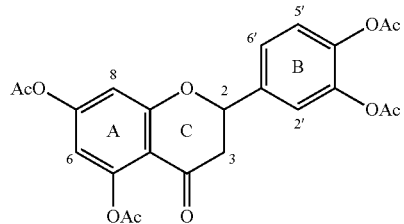

Moreover, an additional compound, trans-4,2',4'-Tri-O-acetylchalcone, Isoliqiuritigenin can be isolated as a peracetate derivative (9) after acetylation and PLC separation from fraction number nine of the roots. This compound is found in many leguminous plants (Roux et al., 1962, *Biochemical Journal*, 82:324).

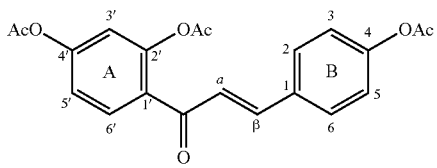

(8) Discussion

Subsequent activity directed purification of only the most active fractions, using column and preparative thin layer chromatography followed by nuclear magnetic resonance (NMR) spectroscopy, and fast atom bombardment (FAB-MS), reveals the universal presence of a novel saponin (1) with strong antifungal activity at a concentration of approximately 125 µg/ml (100-150 µg/ml). Additionally, three flavonoids 5,7,4'-tri-O-flavanone (7), 5,7,3'4'-tetra-O-acetylflavanone (8) and trans-4,2',4'-Tri-O-acetylchalcone (9), showing strong antifungal activity at a concentration of about 625 µg/ml (570-650 µg/ml), can be purified from A. africanus roots.

Semi-purified extracts of the roots and aerial parts of A. africanus obtained by means of solid-liquid extraction with hexane, diethyl ether, ethyl acetate and dichloromethane solvent systems in this order of increasing polarity, variy in antifungal activity. The diethyl ether extraction of the roots is most active in inhibiting the mycelial growth of F. oxysporum, used as test organism in the activity directed purification protocol, while the ethyl acetate extraction of the aerial parts is most active. Although the hexane extraction removes most compounds from both the roots and aerial parts, it is comparably active in both cases.

Following column fractionation of the active liquid-solid extractions, the Q-TLC profiles show diverse chemical constituents in the roots and the aerial plant parts of A. africanus while the latter extract contains comparatively more compounds. However, four active compounds can be isolated from the diethyl ether root extract while only one active compound can be detected in the ethyl acetate aerial part extract. Despite the lower number of active substances in the aerial parts, following different extraction procedures, this fraction is more active in inhibiting the mycelial growth of the test fungus, F. oxysporum.

Compounds purified from the roots and aerial plant parts of A. africanus can be identified by means of $^1$H-NMR and $^{13}$C-NMR spectroscopy. The major compound predominantly isolated from both the roots and aerial plant parts is a novel steroidal saponin with a three sugar chain attached at the C3 position of ring A in the aglycone moiety. The compound can be identified as 3-[O-β-D-glucopyranosyl-(1"-3')-α-L-rhamnosyl-(1"-2')-β-D-glucopyranosyl oxy]agapanthegenin. Previously, a C-3 monoglycosylated saponin, with the same aglycone, was isolated from the root system of A. africanus by both Stephen (1956) and Gonzalez et al. (1974). However, the saponin identified in this study is different with respect to the additionally attached three sugar chain. Sapogenins with a three sugar chain attached are of sporadic occurrence. Additionally, three flavonoids with notable fungicidal activity, 5,7,4'-tri-O-flavanone, 5,7,3'4'-tetra-O-acetylflavanone and trans-4,2',4'-tri-O-acetylchalcone, can be isolated from the roots of A. africanus. Each individual purified flavonoid showed significant in vitro mycelial growth inhibition against F. oxysporum.

The in vitro and in vivo antifungal activity observed with crude and semi-purified extracts of different plant parts of A. africanus seems to be related to the presence of the major compound, a steroidal saponin in all plant parts, as well as the presence of the three flavonoids 5,7,4'-tri-O-flavanone, 5,7,3'4'-tetra-O-acetylflavanone and trans-4,2',4'-Tri-O-acetylchalcone in the root system.

In summary, all four compounds in their pure forms provide an acceptable level of efficacy in inhibiting the mycelial growth of the test fungus in vitro and hold great promise to be applied as one or more natural products in integrated disease management systems in vivo. However, due to a possible synergistic effect of the combined compounds, the application of either a crude or a semi-purified extract might be considered. Importantly, in light of the fact that A. africanus is a perennial, an extract of the combined aerial parts might possess the most potential to be developed into a natural product as harvesting of the above soil parts is non-destructive. This implies that the potential exists for A. africanus to be cultivated as a new crop and to serve as a source for a natural fungicide with broad spectrum control of economically important plant pathogens, especially to small-scale farmers who have no access to synthetic chemicals.

FIGURE LEGENDS

FIG. 1: In vitro inhibitory effect of crude extracts from different plant parts of A. africanus on the mycelial growth of various fungi. Vertical bars indicate standard deviations. Bars designated with different letters indicate significant ($p<0.05$) differences between means according to Duncan's multiple range procedure. Y-axis: mycelial growth inhibition (%). (1)=root; (2)=leaves, (3)=Flower stalks; (4)=Flowers; (5)=above ground plant parts; (6)=reference fungizide FIG. 2: The effect of crude extracts from different plant parts of A. africanus on the respiration rate of a monoculture yeast cells. Vertical bars indicate standard deviations. X-axis: time (min); Y-axis: respiration rate ($cm^3$ $CO_2$ release). 1=roots, 2=flower stalks, 3=above ground plant parts, 4=water, 5=leaves, 6=flowers, 7=ComCat®

Figure 3:
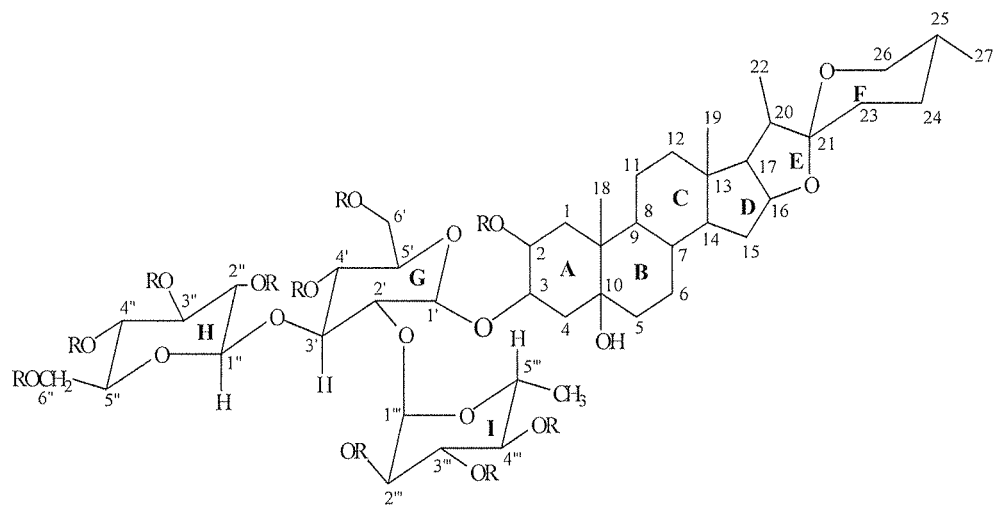
Figure 3:
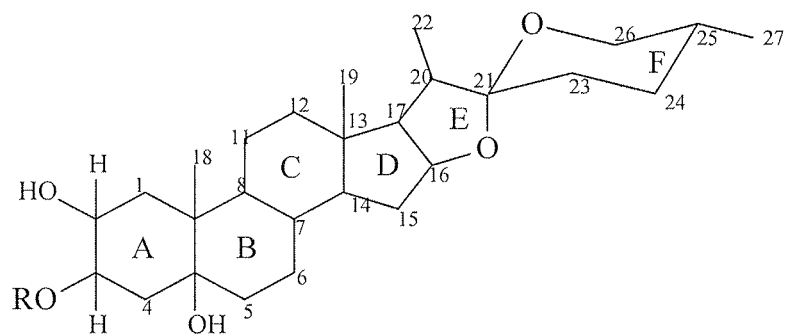

FIG. 3A: Structure of novel saponin (1):
3-[{O-β-D-glucopyranosyl-(1"-3')-α-L-rhamnosyl-(1"-2')}-β-D-glucopyranosyloxy]agapanthegenin.
1: R=H; 2: R=Ac FIG. 3B: Structure of the aglycone (3; agapanthegenin), the glucosylated sapogenin (5) and their respective O-acetyl derivatives (4 and 6).
3: R=H; 4: R=Ac; 5: R=glucose; 6: R=acetyl glucose FIG. 4: NADPH oxidase activity pattern in wheat treated with an Agapanthus extract and a Tulbaghia extract (as reference) according to the invention in dependency of the time after treatment.

FIG. 5: NADPH oxidase activity pattern in sunflower treated with an Agapanthus extract and a Tulbaghia extract (as reference) according to the invention in dependency of the time after treatment.

FIG. 6: peroxidase activity pattern in wheat treated with an Agapanthus extract and a Tulbaghia extract (as reference) according to the invention in dependency of the time after treatment.

FIG. 7: peroxidase activity pattern in sunflower treated with an Agapanthus extract and a Tulbaghia extract (as reference) according to the invention in dependency of the time after treatment.

EXAMPLES

Example 1

Preparation of Crude Extracts

Dried plant material was powdered, using a Retsch SM2000 cutting mill and soaked in 100% methanol (v/g) at a ratio of 2 ml g$^{-1}$ dry weight on a roller mill overnight and the supernatant subsequently decanted. This was repeated five times. The combined suspensions were filtered twice, first under vacuum through a double layer of Whatman filter paper (No. 3 and No. 1) and then by gravity through a single sheet of Whatman No. 1 filter paper. The methanol was removed from the clear supernatant by means of vacuum distillation at 30-35° C. using a Büchi Rotary Evaporator. The remaining aqueous solution was referred to as the crude extract.

Example 2

Preparation of a Dry Powders

Instead of the preparation of a crude extract according to Example 1, the preparation of a dry powder is also applicable. The implication for it is that a considerable reduction in production costs might be achieved and that more hectares of cultivated land can be treated with the product in this form. The preparations of Example 1 and Example 2 show almost identical qualitative and quantitative results with respect to their plant protecting activity/efficacy. Plant material is dried at 35° C., preferably in a drying oven. Dried plant material is first ground to a course powder, using a Retsch SM2000 cutting mill, and subsequently to a fine powder using a special mill than can grind to particles smaller than 100 micron to prevent clogging in a nozzle spray system. The powder is soaked in 100% methanol or ethanol (v/g) at a ratio of preferably 2 ml/g dry weight on a roller mill for 48 h and the bulk of the methanol decanted before the remaining methanol is allowed to evaporate on a large surface. Subsequently, the powder is treated with 100% Ethanol for 24 h in exactly the same way as with methanol. The final product is in the form of a wettable powder that is applied at a rate of preferably 1 g/l and at approximately 300-600 liters per hectare.

Example 3

Screening for Antifungal Properties

A modified agar dilution method (Rios et al. 1988, *Journal of Ethnopharmacology* 23:127-149) was used for determining the inhibition of mycelial radial growth of the test organisms by the plant extracts. All plant pathogenic test fungi were cultured on 2% (m/v) malt agar, prepared according to the specifications of the manufacturers, and autoclaved for 20 min at 121° C. On cooling to 45° C. in a waterbath, 300 µl of a 33% (m/v) Streptomycin solution was added to the basal medium for controlling bacterial growth. Dried material of each plant extract was dissolved in 100 ml sterile distilled water and amended in the agar to yield a final concentration of 1 mg/ml. Working in a laminar flow cabinet, the medium was poured into 90 mm sterile plastic Petri dishes, to a thickness of 2-3 mm, and allowed to set. The center of each test plate was subsequently inoculated with a 5 mm size plug of 7-10 day old cultures, for each of the pathogens separately. A plate containing only the basal medium served as control. Additionally, a plate containing a standard fungicide, carbendazim/difenococnazole (Eria®-187.5 g/l EC), at 1 µg/ml was used as a positive control against each test organism separately to determine the effectiveness of the extracts by comparison. Plates were incubated for four days at 25±2° C. in a growth cabinet. Each assay was performed in triplicate. Radial mycelial growth was determined after four days by calculating the mean of two perpendicular colony diameters for each replicate. The measurement included the assay wells (March et al., 1991, *Zentralbladt fur Mikrobiologie* 146:291-295; Pfaller et al., 1992, *Antimicrobial Agents and Chemotherapy* 36:1805-1809) and was expressed as percentage mycelial growth inhibition by calculating according to the formula of Pandey et al (1982, *Zeitschrift Pflanzenkrankheit and Pflanzenschutz* 89:344-349): (dc−dt)/dc×100, where dc=average diameter of the fungal colony of the negative control and dt=average diameter of the fungal colony treated with the extracts. The data reported were pooled from the two experiments.

Example 4

Screening for Antibacterial Properties

A modified agar diffusion method (Caceres et al., 1993, *Journal of Ethnopharmacology* 38:31-38) was used. Plate count agar (PCA, Biolab) was prepared in the same way as malt agar used in the antifungal screening tests except that the plant extracts were not suspended in the agar. Mother cultures of all plant pathogenic bacteria were sustained on nutritional agar (Caceres et al., 1991, *Journal of Ethnopharmacology* 31:193-208, Rasoanaivo et al., 1993). Overnight soup cultures of the test bacteria were initially prepared separately in sterile 1% (w/v) nutrient broth (Biolab) solutions at 30° C. (Meyer et al, 1995). One hundred µl of each of these bacterial suspensions were subsequently separately transferred to 90 mm Petri dishes containing the sterile PCA agar and evenly streaked on the surface using sterile swabs. Petri dishes were divided into four quarters and a hole, 6 mm in diameter, plunged into the agar of each quarter by means of a sterile cork borer. 50 µl of the 1 mg/ml crude stock solution extracts were transferred into the holes in the agar. The plates were equilibrated at 4° C. for 1 h to allow the extracts to diffuse into the agar before incubation commenced. In this way the development of clear inhibition zones was optimized. Plates were incubated for three days at 25° C. for all plant pathogenic bacteria, but at 35° C. for *M. catharrhalis*. Each assay was performed in duplicate. Inhibition zones were measured using a digital caliper.

Example 5

In Vitro Screening for Bio-Stimulatory Properties of Crude Extracts

Two methods were applied to determine the biostimulatory potential of the organ crude extracts of *A. africanus*.

Method 1: Manometric Method for Determining the Effect of Crude Extracts on the Respiration Rate of a Monoculture Yeast Cells A specially constructed glass respirometer with a short bulged section (reservoir) to contain the yeast cells and a long calibrated tube, closed at the top end to collect $CO_2$ gas, was used in determining the effect of the *A. africanus* crude extracts on the respiration rate of a monoculture yeast cells. Dry baker's yeast (0.8 g) was placed in the reservoir of the respirometer. Subsequently, 70 ml of each of the plant extracts, previously prepared at a concentration of 0.5 mg/ml and containing 5 mg/ml glucose to serve as respiratory substrate for the yeast cells, was added to the respirometer. The apparatus was tilted sideways to release air bubbles trapped in the dry baker's yeast and placed in a water bath pre-heated to 29° C. ComCat®, a commercial biostimulant, was used as a positive control at 0.5 mg/ml (optimum concentration according to the manufacturers; Agraforum, Germany, 2002) and distilled water as a second control. $CO_2$ release by the yeast cells was measured in cm$^3$ at 30 minute intervals over a three hour incubation period by reading the released gas volume from the calibrated tube. Tests were performed in triplicate.

Method 2: The Effect of Different Organ Crude Extracts of *A. africanus* on the Percentage Germination of Radish Seeds and Subsequent Seedling Growth Two sheets of special germination paper (30×30 cm) were used to test the effect of each plant crude extracts of *A. africanus* on the germination of radish seeds as well as the subsequent seedling growth. A line, 10 cm from the top, was drawn on the one sheet and 20 radish seeds spaced evenly on the line. A second sheet of germination paper was placed on top of the first and moistened with either 0.5 mg/ml solutions of the crude extracts, distilled water (negative control) or 0.5 mg/l solution of ComCat® (positive control). Both sheets of paper were rolled up longitudinally and placed upright in Erlenmeyr flasks containing either crude extract, distilled water or the ComCat® solution and kept at 25° C. in a growing chamber in the dark. Seed germination as well as coleoptile and root lengths were determined at 24 h intervals over a 96 h incubation period. Tests were performed in triplicate.

Example 6

Statistical Analysis of Data

Analysis of variance (ANOVA) was performed on the data, using the SAS (1999; SAS/IML software; Version 6; SAS Institute) program, to identify differences between treatments. Duncan's multiple range (DMR) procedure for comparison of means (Steele & Torrie, 1980, *Principles and procedures of statistics*, 2$^{nd}$ Edition. New York: McGraw-Hill.) was applied to separate means (P<0.05).

Example 7

Isolation of *Mycosphaerella pinodes*

*M. pinodes* was isolated from diseased leaves and stems of various winter cultivars of field pea at the time of senescence. Collections of the infected plant material were made from the central and south eastern pea-growing areas of Ethiopia. Pieces of the diseased tissues were surface sterilized for 1 minute in 96% (v/v) ethanol, 3 minutes in a 3.5% (v/v) NaCl solution (Moussart et al., 1998, *European Journal of Plant Pathology* 104:93-102) and 30 seconds in 96% (v/v) ethanol. The tissues were subsequently aseptically transferred to corn meal agar amended with streptomycin (0.3 ml/l) in 9 cm Petri dishes and incubated at 20±1° C. in a growth chamber. Isolates initially obtained from the plant material were then grown on Coon's medium (Ali et al., 1978, *Australian Journal of Agricultural Research* 29:841-849) consisting of 4 g maltose, 2 g $KNO_3$, 1.2 g $MgSO_4$, 2.7 g $KH_2PO_4$ and 20 g agar. Cultures were incubated for 14 days to obtain pycnidiospores. To obtain an isolate derived from a single uninucleate cell, a suspension of pycnidiospores was streaked on 15% water agar, incubated overnight at 20±1° C. and examined under a dissecting microscope (80× magnification). A germ tube arising from one cell of a pycnidiospore was severed and transferred to Coon's agar (Clulow & Lewis, 1992, *Plant Pathology* 41:362-369). Six isolates of *M. pinodes* were obtained. All isolates from a single-spore and cultures were maintained on Coon's agar slants and stored in the dark at 5° C.

Example 8

Preparation of a *M. Pinodes* Spore Suspension

Oat meal agar was prepared by gently heating 30 g of oats in 1 liter distilled water for 1 h, stirring frequently, and subsequently filtering through a fine sieve upon which the volume was readjusted to 1 liter. Twenty g of technical agar and 0.1 g Keltane AP was added to the filtrate to yield a 2% (m/v) agar concentration. The agar was autoclaved for 15 min, poured into Petri dishes and allowed to cool off before inoculation of three oatmeal plates with *M. pinodes* mycelia. Plates were incubated in a 12 h photoperiod incubator at 20° C. for 14 days, to ensure the production of pycnidiospores. To prepare the inoculum (spore suspension), sterile distilled water was added to the 14-day-old cultures dislodging spores gently with a sterile glass rod. The suspension was subsequently filtered through four layers of cheese cloth in order to remove the mycelia and the concentration of pycnidiospores was determined by means of a haemocytometer. The pycnidiospore concentration was adjusted to $1 \times 10^5$ spores per ml (Nasir & Hoppe, 1997, *Annals of Applied Biology* 18:32-33) with sterile distilled water prior to the inoculation of pea leaves.

Example 9

In Vivo Assessment of Crude Extract Phytotoxicity

Pea seeds were planted in plastic pots in Bainsvlei soil and grown in a glasshouse (minimum temperature 18° C.). Four weeks after planting, when the leaflets on the third and fourth nodes were fully expanded, three fourth node leaflets per replicate were removed from the plants, placed on Schleicher and Schull No. 595 filter paper and moistened with 4 ml of sterile distilled water in 9 cm Petri dishes. 30 µl of each of a 0.25, 0.5, 1.0 and 2.0 mg/ml solution of the crude extract were placed separately on each of the three leaves per Petri dish and replicated three times. Treatment of the leaves with water and a standard fungicide (Carbendazim/difenoconazole) served as controls. Petri dishes containing the treated leaflets were incubated at 20° C. in a day/night incubator programmed for a 16 h day cycle while 2 ml sterile distilled water was added daily to keep the filter paper moistened. Six days after treatment, phytotoxicity symptoms were assessed on leaves using a six-category scale [0=symptomless; 1=<5% necrotic flecks; 2=>5% necrotic flecks; 3=<50% of inoculated area necrotic; 4=50-100% of inoculated area necrotic; 5=necrosis spreading beyond inoculated areas] based on stereo microscopic observations (Clulow et al., 1991, *Mycological Research* 95: 817-820).

Example 10

In Vivo Assessment of Crude Extract Antifungal Properties Under Glasshouse Conditions Fourth node pea leaflets were obtained and sustained on moist filter paper in Petri dishes as described for the phytotoxicity assessment test. In vivo control of *M. pinodes* spore infection of the leaves by different concentrations (0.25, 0.5, 1.0 and 2.0 mg/ml) of the aerial plant parts, roots, leaves and flowers of *A. africanus* was followed in two ways namely, by inoculating the leaves with 15 µl of a spore suspension ($1 \times 10^5$ spores/ml; Nasir & Hoppe, 1997, *Annals of Applied Biology* 18:32-33) 30 min before applying the different concentrations of the crude extract separately, and the other way around. A standard fungicide, carbendazim/difenoconazole, currently used against *Ascochyta* blight in peas, as well as leaves inoculated only with the spore suspension, served as controls. Three leaves per Petri dish represented a replicate and the experiment was performed in triplicate. Petri dishes containing the differently treated leaves were incubated at 20°

C., the optimal temperature for *M. pinodes* spore germination in a day/night incubator as illumination is necessary for spore germination (Roger & Tivoli, 1996, *Mycological Research* 100:304-306). After incubation for six days the foliar lesions were measured and leaf damage compared to that of the controls.

Example 11

Seed Treatment

Different lots of sorghum seeds were artificially inoculated with either covered (*Sporisorium sorghi*) or loose (*Sporisorium cruentum*) kernel smuts spores at the rate of 5% (w/w) before application of seed treatments. An aerial crude extract of *A. africanus* was suspended in water at a rate of 2.0 g/l. Sorghum seed lots of 90 g each were treated with 15 ml of the crude extract by mixing thoroughly in a small plastic bag 24 h before planting. A standard synthetic seed dressing fungicide, Thiram (65 W), was applied in the same way at the rate of 0.25% (w/w) per Kg seed and served as a positive control. Sorghum seeds artificially inoculated with both loose or covered smuts spores, but were not treated with the extract or synthetic fungicide, served as a second control.

Example 12

Field Trial

A field trial was conducted under irrigation at Melkassa Research Centre, Ethiopia during 2003. Plots were arranged in a randomised complete block design and treatments were replicated three times. Treated sorghum seeds were planted by hand in five rows, leaving 0.75 cm between rows, in 18.75 m² plots. Standard fertilizer was applied and plots were kept at field capacity by means of furrow irrigation. Disease incidence was recorded as percentage infected plants. Grain yield was determined on the whole plot.

Example 13

Activity Directed Liquid-Solid Extraction

Dried methanolic crude extracts of the roots (268.5 g) and aerial parts (368.83 g) of *A. africanus* were fractionated by means of liquid-solid extraction using hexane (DC=2.0), diethyl ether (DC=4.3), ethyl acetate (DC=6.0) and dichloromethane (DC=8.6) as solvents at a ratio of 2 ml/g crude extract. Extraction was repeated more than 20 times with fresh solvent for each step by shaking vigorously on a mechanical shaker for 10 min. The four fractions were collected separately and evaporated to dryness under vacuum at 35° C. by means of a Büchi rotavapor. The mass of recovered dry material was determined for each fraction. In order to establish the success of the fractionation process, a thin layer chromatography (TLC) profile was obtained for each fraction with a 0.5 mm Silica Gel 60 plate using chloroform:methanol: water (80:20:10) as mobile phase. The mycelial growth inhibitory activity potential of each semi-purified extract was subsequently established using *F. oxysporum* as test organism.

Example 14

Activity Directed Column Chromatography Fractionation

The most active extractants obtained from the liquid-solid extraction procedure were further fractionated using column chromatography. A column (2.6×46 cm) packed with either Sephadex LH20 (Pharmacia) for the root extracts or Silica gel (0.25; Merck, Darmstadt, Germany) for the aerial parts was employed. The residue of the root (7 g) was eluted successively with ethanol (100%) followed by methanol (100%) and a methanol:water (50:50 v/v) mixture. The column chromatographic residue of the aerial plant parts (5 g) was eluted with a gradient solvent system of methanol:chloroform (15:85, 20:80, 25:75, 30:70 and 40:60 v/v). Elution was adjusted at a flow rate of 3 ml/min.

Approximately 120 ml of the root and aerial part eluent were collected. Those column chromatographic fractions that showed similar Q-TLC profile patterns were combined separately. Mycelial growth inhibition of *F. oxysporum* was used to identify active column chromatographic fractions for further purification of the active compounds by means of preparative thin layer chromatography.

Example 15

Preparative Thin Layer Chromatography (PTLC)

The most active combined column chromatography fractions were further purified by means of preparative thin layer chromatography (PTLC) using Silica gel F 1500/LS (1 mm) plates. Fifteen mg of each of the active column fractions were dissolved in 50 μl methanol (100%) and loaded onto the plate by streaking evenly over the baseline with the aid of a glass capillary tube. This was repeated 10 times on 10 different plates to separate compounds from a total of 150 mg of each of the active fractions. The plates were dried in front of a fan between streaking and then developed in a saturated chamber using a chloroform:methanol:water (80:20:10 v/v) solvent system as mobile phase. Detection of compounds was done under UV-light at 254 and 365 nm (Wagner and Bladt, 1996, *Plant Drug Analysis. A thin layer chromatography atlas*. Second edition. Springer, Berlin). Individual compounds were isolated by scraping off the detected zones of the sorbent layer from the plates using a spatula and transferred to Eppendorff vials. The compounds were recovered from the Silica by elution with methanol (100%), followed by centrifugation for five minutes at 12000 r.p.m., and tested for antifungal activity after the methanol was removed by drying at 35° C. in an oven.

Example 16

Qualitative Thin Layer Chromatography (Q-TLC)

Only the most active isolated compounds were again tested for purity in an original analytical thin layer chromatography (TLC) system (Mikes and Chalmers, 1979, *Laboratory handbook of chromatographic and allied methods*. Ellis Horwood Ltd., London) using Silica gel 60 $F_{254}$-aluminium backed and pre-coated plates. Ten to 15 mg of each sample were loaded onto the plates at the baseline and developed in a saturated chamber using either chloroform:methanol:water (80:20:10 v/v) or toluene:acetone:ethyl acetate (7:2:1 v/v; Wagner and Bladt, 1996) as solvent systems. After drying the plates in a stream of air, compounds were either detected under UV-light at 254 and 365 nm or the plates were stained with 5% (v/v) ethanolic $H_2SO_4$ or 1% (m/v) Vanillin (1 g in 100 ml $H_2SO_4$; Wagner and Bladt, 1996). Non-pure compounds were again subjected to preparative TLC acidified with 1% (v/v) HCL until pure compounds were obtained. Only pure compounds that showed the highest antifungal activity were subjected to nuclear magnetic resonance (NMR) spectroscopy in order to identify them and to elucidate their molecular structures.

Example 17

Nuclear Magnetic Resonance (NMR) Spectroscopy

To identify the most bioactive compounds purified from the roots and aerial plant parts and elucidate their molecular structures, isolated compounds were washed repeatedly with acetone to obtain an acceptable level of purity. Subsequently, the compounds were submitted to nuclear magnetic resonance spectroscopy ($^1$H NMR). NMR-spectroscopy was performed on a Bruker 300 MHz DRX 300 spectrometer at 296K (23° C.) with tetramethylsilane (Si(CH3)$_4$; TMS) as the internal standard. The solvents used were deuteriochloroform (CDCl$_3$), or deuterioactetone [(CD$_3$)$_2$CO] as indicated. Chemical shifts were reported in parts per million (ppm) on the δ-scale and coupling constants were given in Hz. The following abbreviations were used: s=singlet, d=doublet, dd=doublet-of-doublets, m=multiplet, br=broadened, t=triplet. All FAB mass spectra were recorded on a VG 70-70E double-focusing mass spectrometer. Circular dichroism (CD) spectra were recorded on a Jasco J-710 spectropolarimeter with methanol as solvent. Structural elucidation was achieved via spectroscopic methods (1D NMR and 2D NMR spectrometry), FAB and EI-MS as well as chemical methods, such as hydrolysis. Due to the complexity of the $^1$H NMR spectrum of the non-derivatised sapogenin, a peracetate derivative (2; FIG. 3A) was used in the structural elucidation. This was achieved via spectroscopic (NMR) and spectrometric (MS) methods, as well as hydrolysis.

The invention claimed is:

1. A method for treating plants comprising applying 0.25 g/L to 2 g/L of a biological plant protective agent to a plant under field or glasshouse conditions, wherein the biological plant protective agent comprises an extract dissolved or suspended in water and wherein the extract is obtained by the following steps:
   (i) drying aerial parts, including flowers, of *Agapanthus africanus* at 30-40° C. to the exclusion of sun light;
   (ii) grinding the dried plant material of part (i) to a grit size less than 0.1 mm;
   (iii) soaking the ground material of part (ii) with methanol to form a suspension/solution;
   (iv) stirring the soaked material of step (iii) and separating the methanol-soluble supernatant;
   (v) evaporating the solvent from the supernatant of part (iv) to obtain a solid phase;
   (vi) soaking said solid phase of part (v) in ethanol;
   (vii) stirring the soaked material of step (vi), separating the ethanol-soluble supernatant and evaporating the solvent from the supernatant to obtain a second solid phase;
   (viii) drying the second solid phase of step (vii) to obtain a dry powder.

2. The method according to claim 1, wherein the biological plant protective agent is an antifungal agent.

3. The method of claim 1, wherein the biological plant protective agent induces systemic acquired resistance (SAR) in said plant.

4. The method of claim 1, wherein the biological plant protective agent is an antifungal agent that inhibits the mycelial growth of fungi.

5. The method of claim 1, wherein after applying the biological plant protective agent, said plant is inoculated with fungal spores, wherein the aerial parts in part (i) further include leaves and stalks and wherein 0.25 g/L to 0.5 g/L of the biological plant protective agent is applied to the plant.

6. The method of claim 1, wherein before applying the biological plant protective agent, the plant is inoculated with fungal spores, wherein the aerial parts in part (i) further include leaves and stalks and wherein 1.0 g/L to 2.0 g/L of the biological plant protective agent is applied to the plant.

7. The method of claim 1, wherein after applying the biological plant protective agent, said plant is inoculated with fungal spores, wherein the aerial parts in part (i) further include leaves and stalks and wherein 1.0 and 2.0 g/L of the biological plant protective agent is applied to the plant.

8. The method of claim 1, wherein the plant is in a crop under field conditions.

9. The method of claim 8 wherein the plant and crop is *Sorghum*.

10. The method of claim 8, wherein said biological plant protective agent inhibits kernel smut disease.

* * * * *